United States Patent
Fei et al.

(10) Patent No.: US 12,121,216 B2
(45) Date of Patent: Oct. 22, 2024

(54) MINIATURE HYPERSPECTRAL IMAGING

(71) Applicant: Board of Regents, The University of Texas System, Austin, TX (US)

(72) Inventors: Baowei Fei, Frisco, TX (US); Naeeme Modir, Richardson, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 292 days.

(21) Appl. No.: 17/670,730

(22) Filed: Feb. 14, 2022

(65) Prior Publication Data

US 2022/0257101 A1 Aug. 18, 2022

Related U.S. Application Data

(60) Provisional application No. 63/149,255, filed on Feb. 13, 2021.

(51) Int. Cl.
*A61B 1/045* (2006.01)
*A61B 1/00* (2006.01)
(Continued)

(52) U.S. Cl.
CPC .......... *A61B 1/045* (2013.01); *A61B 1/00016* (2013.01); *A61B 1/0655* (2022.02);
(Continued)

(58) Field of Classification Search
CPC ... A61B 1/045; A61B 1/00016; A61B 1/0655; A61B 1/0684; A61B 1/00006;
(Continued)

(56) References Cited

U.S. PATENT DOCUMENTS

2003/0028078 A1* 2/2003 Glukhovsky ........ A61B 1/0676
600/109
2005/0062838 A1* 3/2005 Kudou ............... G06K 15/1247
347/130
(Continued)

OTHER PUBLICATIONS

Daisuke Sakota et al. "Hyperspectral imaging of vascular anastomosis associated with blood flow and hemoglobin concentration" 2015 37th Annual International Conference of the IEEE Engineering in Medicine and Biology Society (EMBC), 2015, 4 pages.
(Continued)

*Primary Examiner* — Md M Rahman
(74) *Attorney, Agent, or Firm* — Talem IP Law, LLP

(57) ABSTRACT

A miniaturized device providing hyperspectral imaging in real-time includes a body, a camera within the body, a micro-LED array arranged around the camera within the body, and an imaging controller within the body and coupled to the camera and the micro-LED array. The micro-LED array includes micro-LEDs of varying spectral bands. A method for controlling an imaging device includes providing LED timing information and LED intensity information to a micro-LED array, providing camera timing information to a camera for capturing a plurality of images, and receiving the plurality of images from the camera. The timing information includes a timing signal to each micro-LED of the micro-LED array and each timing signal includes a pulse. An image of the plurality of images is captured for a time period associated with each timing signal.

20 Claims, 15 Drawing Sheets

(51) Int. Cl.
A61B 1/06 (2006.01)
G01J 3/28 (2006.01)
(52) U.S. Cl.
CPC .......... A61B 1/0684 (2013.01); G01J 3/2823 (2013.01); *G01J 2003/2826* (2013.01)
(58) Field of Classification Search
CPC ... A61B 1/0607; A61B 1/0638; A61B 1/0676; A61B 1/051; G01J 3/2823; G01J 2003/2826
USPC ........................................................ 356/326
See application file for complete search history.

(56) References Cited

U.S. PATENT DOCUMENTS

2020/0237229 A1    7/2020  Fei
2020/0305723 A1*  10/2020  Eberlin .............. G01N 33/4833
2021/0112647 A1*   4/2021  Coleman ................ G01S 7/497

OTHER PUBLICATIONS

Rutger M. Schols et al. "Differentiation Between Nerve and Adipose Tissue Using Wide-Band (350-1,830nm) in vivo Diffuse Reflectance Spectroscopy" Lasers in Surgery and Medicine, Jun. 4, 2014, 8 pages.

Rebecca L. Siegel et al., "Cancer statistics, 2021," CA: a cancer journal for clinicians, Jan./Feb. 2021, 24 pages.

Shyam Menon et al., "How commonly is upper gastrointestinal cancer missed at endoscopy? A meta-analysis," Endoscopy international open, May 7, 2014, 5 pages.

Georgina Chadwick, et al., "Gastric cancers missed during endoscopy in England," Clinical gastroenterology and hepatology, Jul. 2015, 8 pages.

Guolan Lu et al. "Medical hyperspectral imaging: a review," Journal of biomedical optics, Jan. 2014, 24 pages.

Ningliang Liu, et al., "Gastric cancer diagnosis using hyperspectral imaging with principal component analysis and spectral angle mapper," Journal of Biomedical Optics, Jun. 27, 2020, 9 pages.

Hamed Akbari, et al., "Cancer detection using infrared hyperspectral imaging," Cancer science, Apr. 2011, 6 pages.

Zhimin Han, et al., "In vivo use of hyperspectral imaging to develop a noncontact endoscopic diagnosis support system for malignant colorectal tumors," Journal of biomedical optics, Jan. 6, 2016, 9 pages.

Hoong-Ta Lim et al., "A four-dimensional snapshot hyperspectral video-endoscope for bio-imaging applications," Scientific reports, Apr. 5, 2016, 10 pages.

Robert T. Kester et al., "Real-time snapshot hyperspectral imaging endoscope," Journal of biomedical optics, May 10, 2011, 13 pages.

Lan-Rong Dung et al., "A wireless narrowband imaging chip for capsule endoscope," IEEE Transactions on Biomedical Circuits and Systems, Nov. 11, 2010, 7 pages.

Jonathan Shapey et al., "Intraoperative multispectral and hyperspectral label-free imaging: A systematic review of in vivo clinical studies," Journal of biophotonics, 2019, 13 pages.

Raju Shrestha et al., "How are LED illumination based multispectral imaging systems influenced by different factors?," International Conference on Image and Signal Processing, 2014, 11 pages.

K. S. Choi et al. "Effect of endoscopy screening on stage at gastric cancer diagnosis: results of the National Cancer Screening Programme in Korea" British Journal of Cancer, Dec. 9, 2014, 5 pages.

Dimitris K. Iakovidis et al. "Towards Intelligent Capsules for Robust Wireless Endoscopic Imaging of the Gut" IEEE International Conference on Imaging Systems and Techniques, Oct. 2014, 7 pages.

Le Qiu et al. "Multispectral light scattering endoscopic imaging of esophageal precancer" Light: Science & Applications, Apr. 6, 2018, 10 pages.

Larisa A. Zherdeva et al. "In vivo hyperspectral imaging and differentiation of skin cancer" Optics in Health Care and Biomedical Optics VII, Nov. 2016, 9 pages.

David T. Dicker et al. "Differentiation of normal skin and melanoma using high resolution hyperspectral imaging" Cancer Biology & Therapy, May 26, 2006, 7 pages.

Georgios N. Stamatas et al. "Hyperspectral Image Acquisition and Analysis of Skin" Proceedings of SPIE—The International Society for Optical Engineering, Jul. 2003, 7 pages.

H. Köhler et al. "Hyperspectral imaging (HSI) for intraoperative spatially resolved quantification of the fat content of tissue" Retrieved on: Feb. 14, 2023, 4 pages, Retrieved from: https://www.researchgate.net/profile/Hannes_Koehler5/publication/337716674_Qantification_of_fat_contained_in_tissuepdf/data/5de674b7299bf10bc33d41b4/Qantification-of-fat-contained-in-tissue.pdf.

Guolan Lu et al. "Detection of Head and Neck Cancer in Surgical Specimens Using Quantitative Hyperspectral Imaging" Clinical Cancer Research, Sep. 15, 2017, 11 pages.

* cited by examiner

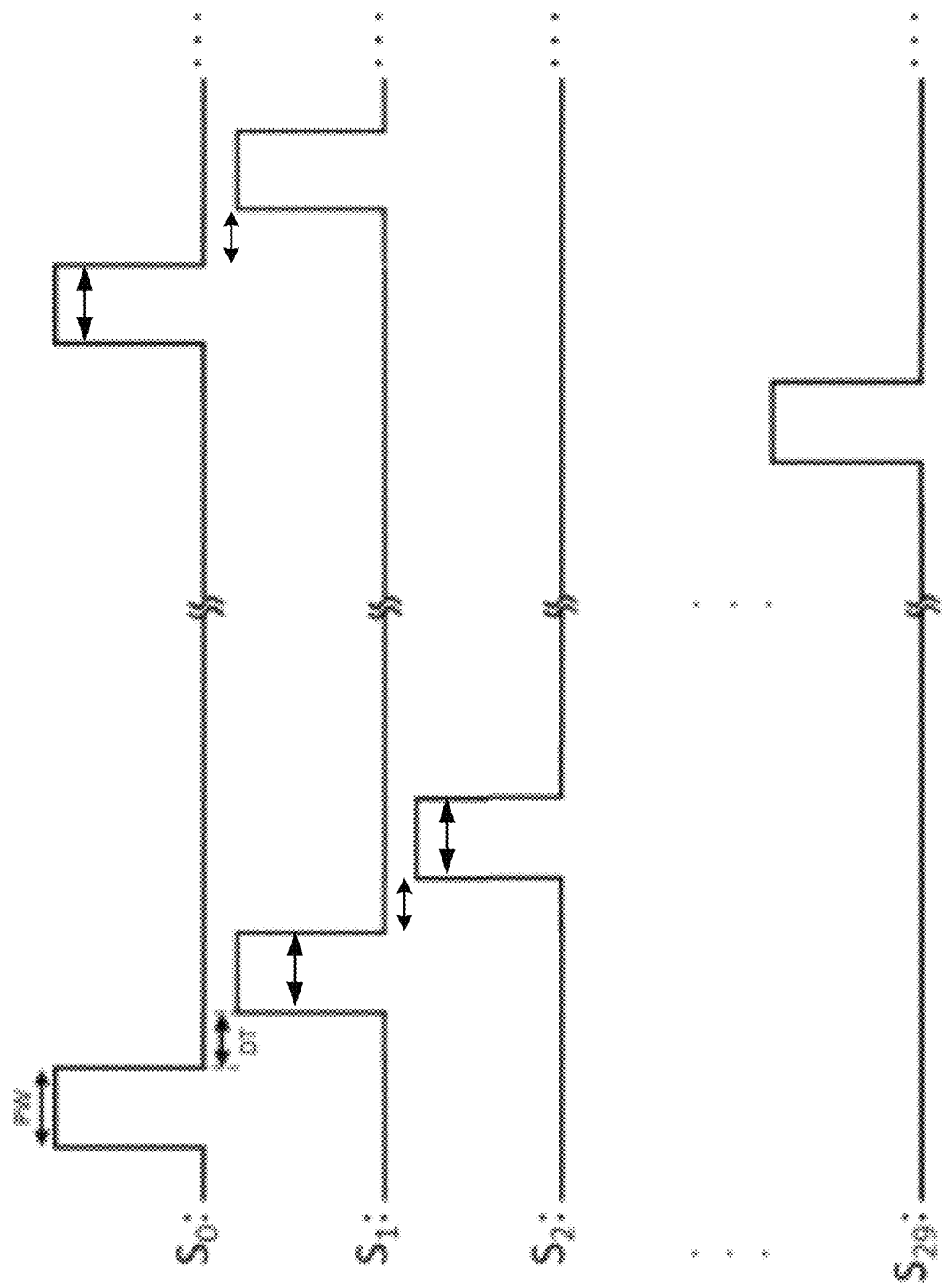

MINIATURE HYPERSPECTRAL IMAGING

CROSS-REFERENCE TO RELATED APPLICATION

This application claims the benefit of U.S. Provisional Application Ser. No. 63/149,255, filed Feb. 13, 2021.

BACKGROUND

Identification and treatment for gastrointestinal (GI) diseases has been improved by the use of endoscopic imaging. However, although extensive utilization of endoscopic imaging in the 2000's led to a rapid decline in incident rates of gastrointestinal diseases such as colorectal cancer, digestive system cancers still rank as the highest among all cancers in incidence and mortality in the United States.

Conventional endoscopy uses RGB (red-green-blue) light and/or white light to generate reflectance images of surface tissues and/or internal organs to assess appearance (e.g., tissue color, surface, morphology). However, the poor spectral resolution over a large number of bands for each channel and/or a small number of bands for each channel provides poor image quality and prevents the identification of tumors that are invisible to conventional color cameras, resulting in approximately 10% of cancers being missed during upper GI endoscopy.

Research has shown that multispectral imaging (MSI) or hyperspectral imaging (HSI) improves diagnosis of cancerous tissue by improving spectral resolution using different discrete wavelengths or spectral bands of light to capture images, which are used to differentiate normal tissue from cancerous tissue. Indeed, MSI/HSI has proven to be effective in visualizing tumors that are invisible to conventional color cameras. HSI differs from MSI on the number of spectral bands used. Typically, MSI involves fewer than 20 discrete spectral bands, while HSI involves at least 20 discrete spectral bands.

There are four main types of MSI/HSI techniques; point scanning, line scanning (pushbroom), wavelength scanning, and snapshot. Point scanning and line scanning (pushbroom) approaches are slow but can provide high spectral and spatial resolution. Snapshot scanning can be fast but is limited in terms of the spectral resolution and the number of wavelengths. Wavelength scanning provides relatively high speed and high spectral and spatial resolutions. In endoscopic imaging, a real-time or rapid (close to real-time) imaging rate is preferred for visual identification of disease. Therefore, wavelength scanning and/or snapshot scanning approaches are more useful than point or line scanning for MSI/HSI endoscopy. Currently, systems using wavelength scanning and/or snapshot scanning approaches suffer from various limitations, including limited spectral resolution, small field of views that are not useful for large-scale visualization needed for certain applications such as GI endoscopy and/or laparoscopy, limited movement of the device due to optical fiber use for lighting, cameras that are too big for use in certain applications, and in cameras that are small enough to be used in certain applications, inadequate frame rate and/or poor image quality.

BRIEF SUMMARY

Miniature hyperspectral imaging methods and systems are provided. The HSI methods and systems described herein use a micro-LED array with varying wavelengths as the illumination source, a miniaturized, high-speed camera for capturing images, and an imaging controller coupled to the micro-LED array and the camera to provide LED timing information, LED intensity information, and camera timing information for indicating when to capture images. Advantageously, real-time or rapid imaging with high spectral and spatial resolutions are achieved in a device that is suitable (e.g., small enough and provides enough range of movement) for use in certain applications, such GI endoscopy, laparoscopy, and/or handheld applications.

A miniaturized hyperspectral imaging device providing imaging in rapid or real-time includes a body, a camera within the body, a micro-LED array within the body, and an imaging controller within the body and coupled to both the camera and the micro-LED array. The micro-LED array includes micro-LEDs of varying spectral bands. The imaging controller provides LED timing information and LED intensity information to the micro-LED array.

A method for controlling an imaging device includes providing LED timing information and LED intensity information to a micro-LED array, providing camera timing information to a camera for capturing a plurality of images, and receiving the plurality of images from the camera. The micro-LED array includes micro-LEDs of varying spectral bands and the plurality of images can include images corresponding to the various spectral bands. The LED timing information includes a timing signal to each micro-LED of the micro-LED array. The camera timing information includes a camera timing signal related to each timing signal for the micro-LEDs such that an image can be captured for a time period associated with each timing signal.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIGS. 6A-6C illustrate forward pulse signals sent to a micro-LED array.

DETAILED DESCRIPTION

Miniature hyperspectral imaging methods and systems are provided. The HSI methods and systems described herein use a micro-LED array with varying wavelengths as the illumination source, a miniaturized, high-speed camera for capturing images, and an imaging controller coupled to the micro-LED array and the camera to provide LED timing information, LED intensity information, and camera timing information for indicating when to capture images. Advantageously, real-time or rapid imaging with high spectral and spatial resolutions are achieved in a device that is suitable (e.g., small enough and provides enough range of movement) for use in certain applications, such GI endoscopy, laparoscopy, and/or handheld applications.

A miniaturized hyperspectral imaging device providing imaging in rapid or real-time includes a body, a camera within the body, and a micro-LED array arranged around the camera within the body. An imaging controller is also provided within the body and coupled to the camera and the micro-LED array. The micro-LED array includes micro-LEDs of varying spectral bands. The imaging controller provides LED timing information and LED intensity information to the micro-LED array.

Spatial and spectral resolutions are two main factors that can define the quality of an HSI device. As described herein, spatial resolution is defined as the surface area imaged by one pixel of a sensor. High spatial resolution corresponds to small pixel size, and means each pixel represents a relatively small surface area, providing greater detail in an image. That is, the higher the spatial resolution, the more detail the image will contain. In some cases, the HSI system can provide a spatial resolution of at least 0.005 mm, such as at least 0.010 mm, at least 0.015 mm, or at least 0.20 mm.

As described herein, spectral resolution is defined as the spectral content which is detected by the HSI system. Spectral resolution can be characterized by the number or choice of spectral bands (red, green, blue, NIR, SWIR, thermal, specific LEDs etc.), the spectral distribution of optical power of each spectral band, the width of each spectral band and which spectral bands (or combinations thereof) are desired for identifying specific features. A set of narrow band micro-LEDs including two or more distinct spectral bands, the combination of which span the spectral range of the spectral resolution, can provide an ability of the system to distinguish material characteristics between the two or more distinct spectral bands. Spectral range of the HSI system, as a whole, can be defined as the range of the electromagnetic spectrum capable of being imaged, typically from the ultraviolet to the infrared region.

Figure 1:
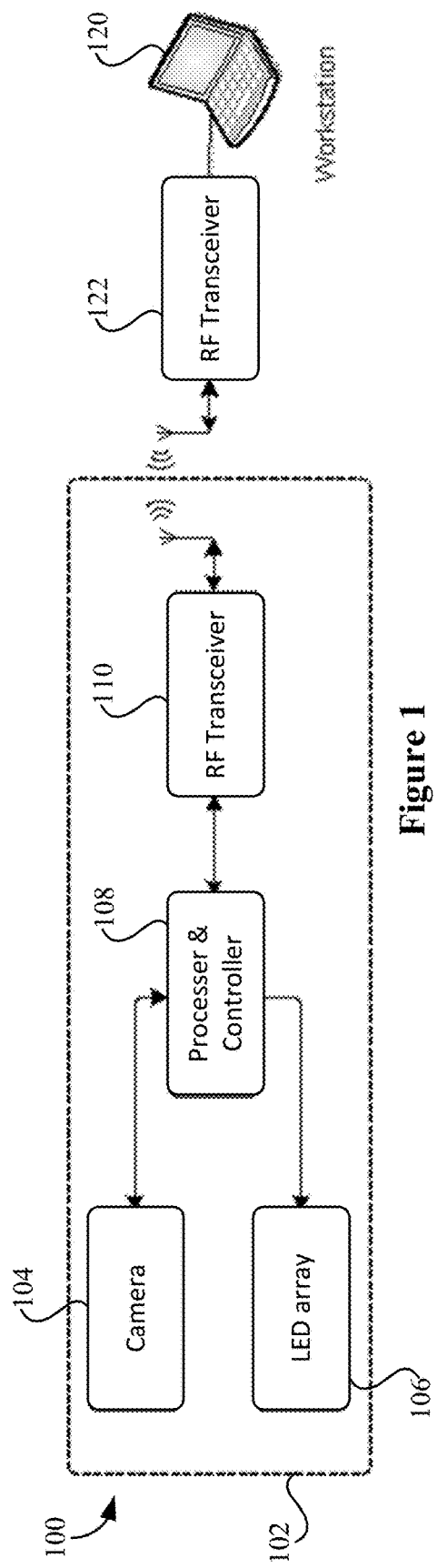
FIG. 1 illustrates a block diagram of a hyperspectral imaging system.

FIG. 1 illustrates a block diagram of a hyperspectral imaging (HSI) system.

Referring to FIG. 1, an HSI system 100 includes an HSI device 102. The HSI device 102 includes a camera 104, a micro-LED array 106, and an imaging controller 108. The imaging controller 108 provides LED timing information (e.g., a timing signal to each micro-LED of the micro-LED array) and LED intensity information to the micro-LED array 106. The micro-LED array 106 can include micro-LEDs having at least 8 varying spectral bands. In some cases, at least 16 varying spectral bands are provided. In some cases, at least 20 varying spectral bands are provided. In some cases, at least 30 varying spectral bands are provided. Of course, more or fewer varying spectral bands may be used; however, the ability to have at least eight varying spectral bands in such a small form factor enables a variety of imaging capabilities.

The imaging controller 108 may further provide camera timing information to the camera 104 that indicates when to capture an image (e.g., to capture an image during a time period associated with each timing signal). In some cases, the HSI device 102 may be included in a catheter for insertion into a patient's body for imaging. In some cases, the HSI device 102 has a body configured as an endoscope. In some cases, the HSI device 102 has a body configured as a laparoscope. In some cases, the HSI device 102 has a body configured as a handheld device. Other configurations are also possible.

In some cases, the HSI device 102 further includes a transceiver 110 to wirelessly communicate with other devices while at least a portion of the HSI device 102 is inside a patient's body. The transceiver 110 may support one or more wireless protocols such as Bluetooth®, Zigbee®, Near Field Communication (NFC), etc.

In some cases (e.g., as illustrated in FIG. 1), the HSI system 100 further includes an external workstation 120. For example, the external workstation 120 may include a display (e.g., for displaying images captured by the camera 104 of the HSI device 102). In some cases, the external workstation 120 further includes a computer for processing the images captured by the camera 104 of the HSI device 102. In some cases, the computer of the external workstation 120 provides control commands (e.g., timing signals for the micro-LED array 106 and/or camera timing information for the camera 104) to the imaging controller 108.

In some cases, the external workstation 120 further includes a workstation transceiver 122 to communicate (e.g., to transmit control commands and/or receive images) with the HSI device 102. In some cases, the HSI transceiver 110 and the workstation transceiver 122 are radio frequency (RF) transceivers. In some cases, the workstation transceiver 122 is integrated into the computer; in some cases, the workstation transceiver is separate from the computer.

Figure 2:
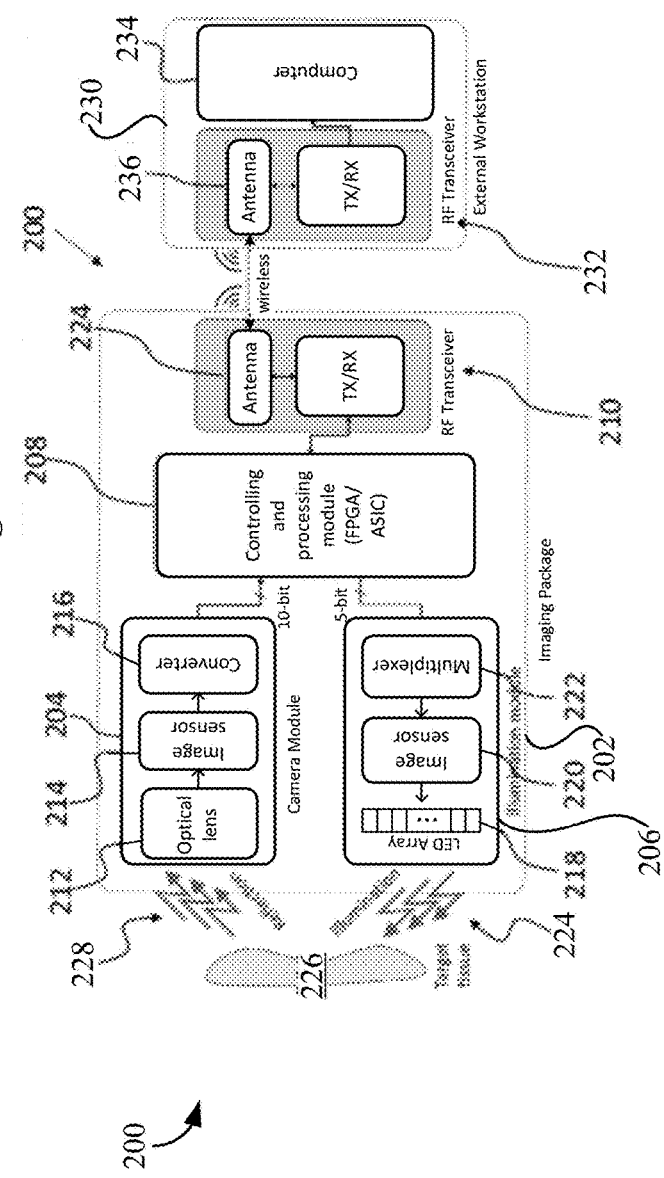
FIG. 2 illustrates a block diagram of an embodiment of a hyperspectral endoscopic system.

FIG. 2 illustrates a block diagram of an embodiment of a hyperspectral endoscopic system. The embodiment of the HSE system of FIG. 2 is an example implementation of the HSI system illustrated in FIG. 1. Referring to FIG. 2, an HSE system 200 can include an HSE device 202 and an external workstation 230. The HSE device 202 includes a camera module 204, an illumination module 206, an imaging controller 208, and an HSE transceiver 210. The imaging controller 208 provides LED timing information and LED intensity information to the illumination module 206 and camera timing information to the camera module 204. The camera module 204 includes an optical lens 212, an image sensor 214, and a converter 216. The illumination module 206 includes a micro-LED array 218, voltage adjustment 220, and a multiplexer 222. During operation, the illumination module 206 can provide illumination 224 (e.g., via the micro-LED array 218) directed towards a target tissue 226 (e.g., a GI tract of a patient) and the camera module 204 can receive reflection 228 of the illumination 224 reflecting off the target tissue 226 to capture images.

In some cases, the micro-LED array 218 is a multispectral band micro-LED array. In some cases, the LED timing information sent from the imaging controller 208 to the illumination module 206/micro-LED array 218 includes a timing signal to each micro-LED of the micro-LED array 218, with each timing signal having a pulse. In some cases, the LED intensity information sent from the imaging controller 208 to the illumination module 206/micro-LED array 218 includes a particular forward voltage for each timing signal, which can be accomplished using a potentiometer (e.g., via the voltage adjustment 220). In some cases, the LED intensity information sent from the imaging controller 208 to the illumination module 206/micro-LED array 218 includes a corresponding pulse duration of the pulse for each timing signal, which can be accomplished using a pulse-width modulator (PWM) and/or a pulse-density modulator (PDM). In such cases, the voltage adjustment 220 may or may not be omitted. In some cases, the imaging controller 208 is a field-programmable gate array (FPGA). In some cases, the imaging controller 208 is an application-specific integrated circuit (ASIC). In some cases, the imaging controller 208 can be integrated as a system-on-chip (SoC) that generates appropriate signals based on commands received from the external workstation 230 for controlling the illumination module 206/micro-LED array 218 and the camera module 204.

In some cases, the camera module 204 can be a high-speed micro digital camera with a monochrome sensor (e.g., image sensor 214) that captures a series of images from a region of interest (ROI), with each image being captured during illumination of a spectral band (e.g., discrete or complex) that is emitted from the micro-LED array 218 under timing control of the imaging controller 208. In some cases, the camera module 204 has a frame rate of the camera (FRc) of at least two hundred frames per second, such as at least three hundred frames per second, at least four hundred frames per second, at least five hundred frames per second, at least six hundred frames per second, or at least seven hundred frames per second. The imaging rate of the device ($FR_{MS}$) can be calculated using the formula:

$$FR_{MS} = \frac{FR_C}{\Lambda},$$

where $\Lambda$ represents the number of discrete spectral bands and/or wavelengths provided by the LEDs or subset of micro-LEDs in the micro-LED array 218, with each discrete spectral band being a spectral width of illumination output of each LED. For example, with thirty micro-LEDs in the micro-LED array 218 or thirty different subsets of micro-LEDs in the micro-LED array 218 (with each micro-LED and/or subset of micro-LEDs being illuminated one-at-a-time) and a FRC of 600 frames per second, the imaging rate of the HSE device 202 is 20 frames per second (e.g., 20 fps=600 fps/30).

In some cases, the HSE system 200 is configured to provide a frame rate equal to or greater than five fps, such as equal to or greater than six fps, equal to or greater than seven fps, equal to or greater than eight fps, equal to or greater than nine fps, equal to or greater than ten fps, equal to or greater than eleven fps, equal to or greater than twelve fps, equal to or greater than thirteen fps, equal to or greater than fourteen fps, equal to or greater than fifteen fps, equal to or greater than sixteen fps, equal to or greater than seventeen fps, equal to or greater than eighteen fps, equal to or greater than nineteen fps, equal to or greater than twenty fps, equal to or greater than twenty-one fps, equal to or greater than twenty-two fps, equal to or greater than twenty-three fps, equal to or greater than twenty-four fps, equal to or greater than twenty-five fps, equal to or greater than twenty-six fps, equal to or greater than twenty-seven fps, equal to or greater than twenty-eight fps, equal to or greater than twenty-nine fps, or equal to or greater than thirty fps.

The proposed system can capture images with higher resolution; however, the bottleneck can be the data rate. To address this challenge, two modes of resolution for the system can be implemented. One mode is real-time with lower resolution for live monitoring, and the other mode is high resolution with a lower frame rate for capturing diagnosis hyperdata. As an illustrative example as provided by a prototype, in real-time mode, the resolution is 0.2 mm over 20 mm by 20 mm FOV; and in slow mode, the resolution could be improved based on the frame rate. For example, for 2 fps the resolution could be 0.02 mm.

As a specific example, the effective field of view (FOV) of the camera module 204 can be equal to or greater than twenty millimeters by twenty millimeters with a spatial resolution of less than or equal to 0.2 millimeters and an image size of at least one hundred pixels by one hundred pixels. In some cases, the effective FOV is at least twenty-five millimeters by twenty-five millimeters, such as equal to or greater than thirty millimeters by thirty millimeters, equal to or greater than forty millimeters by forty millimeters, equal to or greater than forty-five millimeters by forty-five millimeters or equal to or greater than fifty millimeters by fifty millimeters. In some cases, the spatial resolution is less than or equal to 0.2 millimeters, such as less than or equal to 0.018 millimeters, less than or equal to 0.015 millimeters, less than or equal to 0.013 millimeters, less than or equal to 0.010 millimeters, or less than or equal to 0.0098 millimeters. In some cases, the image size is greater than or equal to one hundred pixels by one hundred pixels, such as greater than or equal to two hundred by two hundred pixels, greater than or equal to three hundred by three hundred pixels, greater than or equal to four hundred by four hundred pixels, greater than or equal to five hundred by five hundred pixels, or greater than or equal to five hundred twelve hundred by five hundred twelve hundred pixels. As a specific example, the FOV can be fifty millimeters by fifty millimeters and the image size can be five hundred twelve by five hundred twelve, resulting in a pixel size of about 0.098 millimeters.

The FOV, resolution, and image size or spatial resolution can be within any range of values disclosed herein and can be combined with any other aspect described herein.

The external workstation 230 includes a workstation transceiver 232 and a computer 234. The computer 234 can include a desktop computer, laptop computer, handheld device (e.g., smart device such as an iPhone or iPad), remotely networked computing system, and/or any computing system known in the field to include adequate computing power required for HSE image processing. The image processing performed by the computer 234 can include image denoising, image channel integration, and/or image classification. The workstation transceiver 232 can include a workstation transceiver antenna 236. Similarly, the HSE transceiver 210 can include an HSE transceiver antenna 229, which may be positioned at a tip of the HSE device 202. In some cases, the HSE transceiver 210 and/or the workstation transceiver 232 are RF transceivers. To avoid power losses, a matching network can be used as an interface between the transceiver 210, 232 and the antenna 229, 236.

In some cases, the frequency band of either transceiver 210, 232 is 2.4 GHz. Therefore, the transceivers 210, 232 work in Industrial, Scientific, and Medical (ISM) bands. The minimum required data bandwidth ($BW_{minm}$) in Mega bit per second can be measured based on the number of discrete spectral bands ($\Lambda$), frame size (M×N), imaging frame rate ($FR_{MS}$), and dynamic range (L), with the resulting formula being:

$$BW\min = \frac{\Lambda \times M \times N \times L \times FR_{MS}}{2^{20}}$$

Therefore, for a spectral resolution of thirty spectral bands, each band being a spectral width of illumination output of each LED, an image size of two hundred fifty-six by two hundred fifty-six pixels, a frame rate of 20 fps, and a dynamic range of 8 bits, the data bandwidth is calculated to be 300 Mega bit per second.

Although the above examples describe an HSE system, HSI imaging can be provided in a miniaturized wireless device that include endoscopic, laparoscopic, and handheld devices that can be used to image and differentiate between a wide range of healthy, benign, and malignant tissues.

Figure 3A:
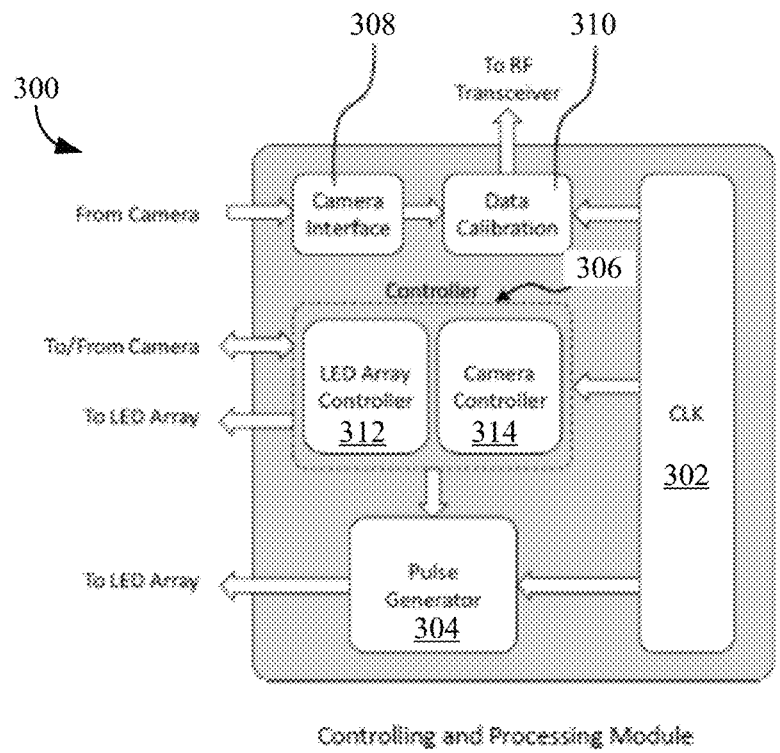
FIG. 3A illustrates a block diagram of a specific embodiment of an imaging controller.

FIG. 3A illustrates a block diagram of a specific embodiment of an imaging controller, such as imaging controller 108 of FIG. 1 and/or imaging controller 208 of FIG. 2. Referring to FIG. 3A, an imaging controller 300 includes a CLK 302 (e.g., a clock), a pulse generator 304, a controller module 306, a camera interface 308, and a data calibration processor 310. The controller module 306 includes an LED array control portion 312 and a camera control portion 314. During operation, the CLK 302 can provide signals (e.g., timing signals) to the pulse generator 304 and the controller module 306. The pulse generator 304 can receive signals from both the CLK 302 and the controller module 306, and provide pulse signals to the micro-LED array. The controller module 306 can provide signals (e.g., camera timing information for indicating when to capture an image) and receive signals from a camera and provide signals (e.g., LED timing information and LED intensity information) to a micro-LED array. The camera interface 308 can receive signals from the camera (e.g., signals that include image data of captured images) and provide those signals to the data calibration processor 310. The data calibration processor 310 can transmit image data of captured images to an external workstation for image processing.

Figure 3B:
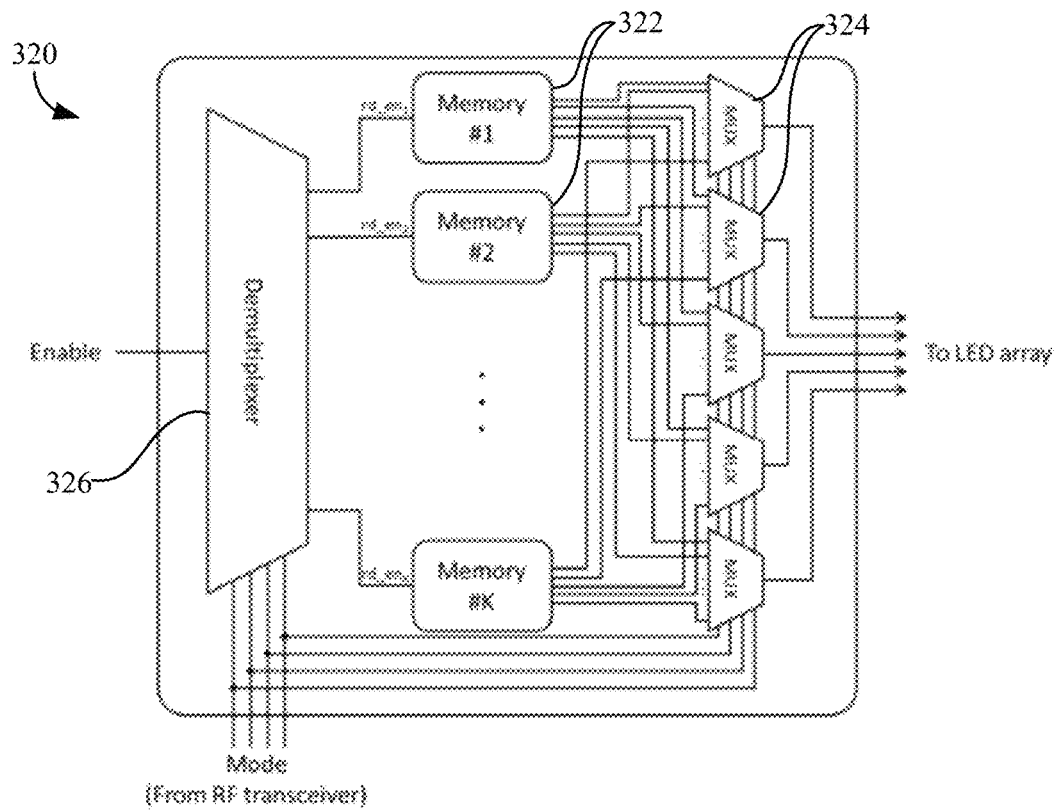
FIG. 3B illustrates a block diagram of an LED control portion of an imaging controller.

FIG. 3B illustrates a block diagram of an LED control portion of an imaging controller, such as LED control portion 312 of FIG. 3A. Referring to FIG. 3B, an LED control portion 320 can includes K memory units 322, with each memory unit 322 including a defined controlling sequencing mode for a number of micro-LEDs in a micro-LED array. The number of micro-LEDs may be different than or the same as the number of mux units 324. The number of mux units 324 may be different than or the same as the number K of memory units 322. The memory units 322 are enabled by a demultiplexer 326, which utilizes a set of mode inputs that are received via a transceiver (e.g., HSI transceiver 110 of FIG. 1 and/or HSE transceiver 210 of FIG. 2). The mode inputs drive the demultiplexer 326 and the mux units 324 to energize one or more micro-LEDs of the micro-LED array in a time sequence.

Figure 3C:
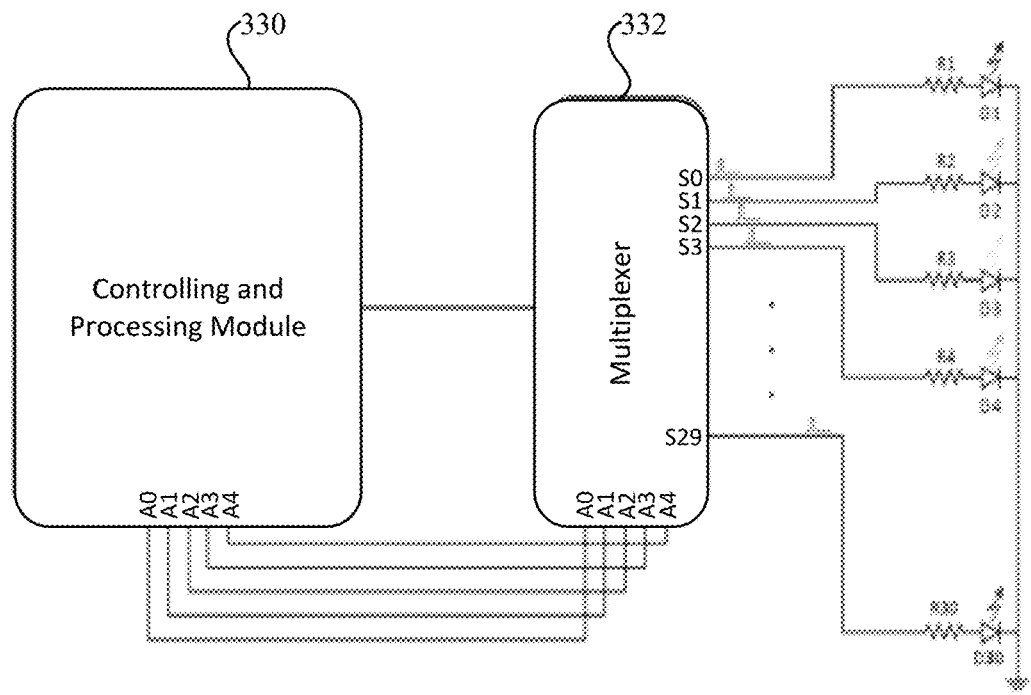
FIG. 3C illustrates a block diagram of connections between an imaging controller coupled to a multiplexer coupled to thirty micro-LEDs.

FIG. 3C illustrates a block diagram of connections between an imaging controller coupled to a multiplexer coupled to thirty micro-LEDs. Referring to FIG. 3C, an imaging controller 330 coupled to a multiplexer 332, which is coupled to thirty micro-LEDs of an LED array, provides illumination for real-time or rapid HSE imaging. Each of the thirty micro-LEDs provide a discrete spectral band that may or may not overlap with one or more of the other micro-LEDs of the micro-LED array. In some cases, a subset of the thirty micro-LEDs can be illuminated simultaneously with varying intensities to create complex spectral bands containing multiple wavelengths of interest for imaging patient tissue(s). The micro-LEDs having discrete spectral bands and/or subset of micro-LEDs creating complex spectral bands may be illuminated in a time sequence for a camera to capture reflection images of the illuminated patient tissue(s). For example, LED timing information provided by the imaging controller 330 to the micro-LED array (e.g., via the multiplexer) includes a timing signal to each LED of the LED array, with each timing signal having a pulse. A time delay between a first timing signal sent to a first micro-LED or subset of micro-LEDs of the micro-LED array and a subsequent timing signal sent to a second micro-LED of second subset of micro-LEDs of the micro-LED array is optimized for minimum time and minimum interference between illuminations of the LEDs, as is explained in detail below with respect to FIGS. 6A-6C.

Figure 4A:
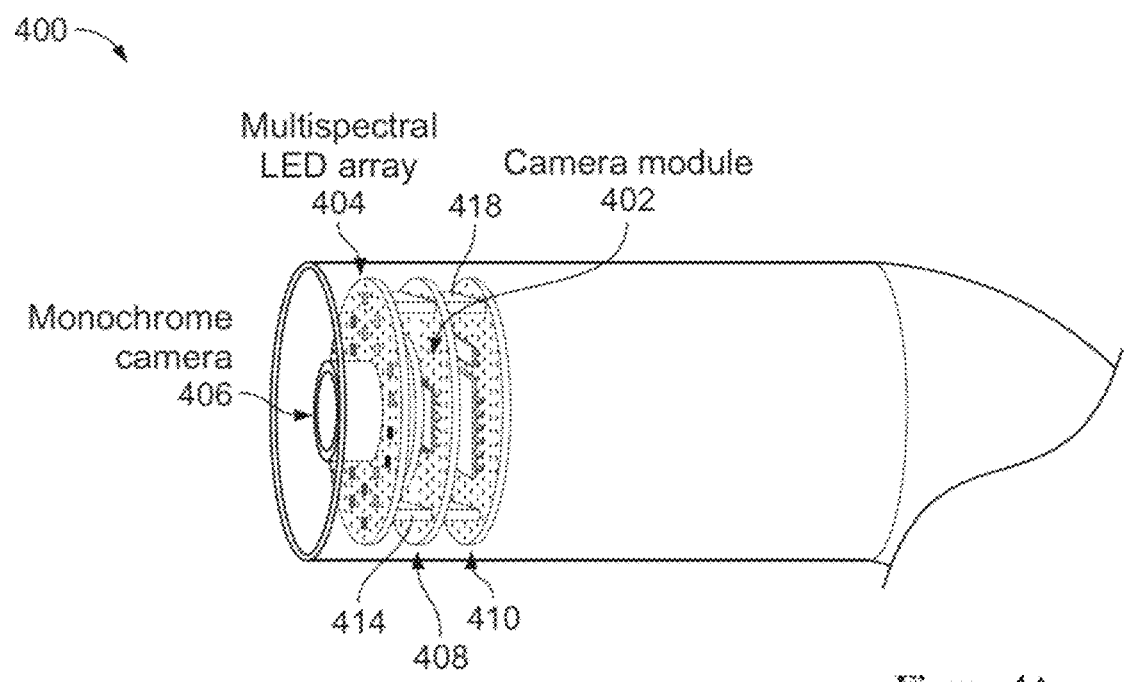
FIG. 4A illustrates an angled view of a hyperspectral endoscopic catheter.
Figure 4B:
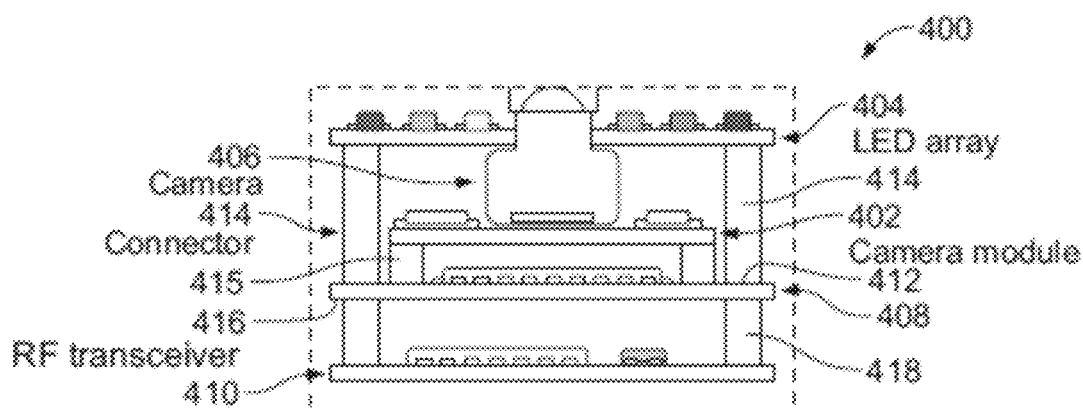
FIG. 4B illustrates a side view of a hyperspectral endoscopic catheter.

FIG. 4A illustrates an angled view of a hyperspectral endoscopic catheter; and FIG. 4B illustrates a side view of a hyperspectral endoscopic catheter. Referring to FIGS. 4A and 4B, an HSE catheter 400 houses a system that includes a camera module 402, a micro-LED array 404, a camera 406, an imaging controller 408, and an HSE transceiver 410. The system can be packaged as a 3D integrated circuit system to achieve a smaller footprint. For example, in some cases, each functional component can be arranged on its own board and the boards coupled together. In some cases, dies containing the functional components can be stacked with optional interposers and electrically connected via through silicon vias and/or other known coupling mechanisms. In the illustrated example, the micro-LED array 404 is provided on a board with an aperture to enable the camera 406 to have its lens extend therethrough. The camera 406 is disposed on a board with a camera module 402 (e.g., appropriate camera circuitry) that has a smaller area than the board with the micro-LED array 404 so the board with the micro-LED array 404 can be coupled to a first side 412 of a third board third board with the imaging controller 408 via connectors 414 near an outer perimeter of the third board while the board with the camera module 402 is coupled to the first side 412 of the third board via connectors 415. The stack of micro-LED array 404, camera 406 and camera module 402, and imaging controller 408 can be coupled from the second side of the third board to a board with the RF transceiver 410 via connectors 418.

Connectors 414, 418 can function as mechanical connectors and/or electrical connectors. Electrical connectors are suitable to support communication between the various components, including the micro-LED array 404, the camera 406, the imaging controller 408, and the HSE transceiver 410. The micro-LED array 404 can be a multispectral micro-LED array or a hyperspectral LED array. In some cases, the camera 406 is a high speed monochrome camera.

Figure 5A:
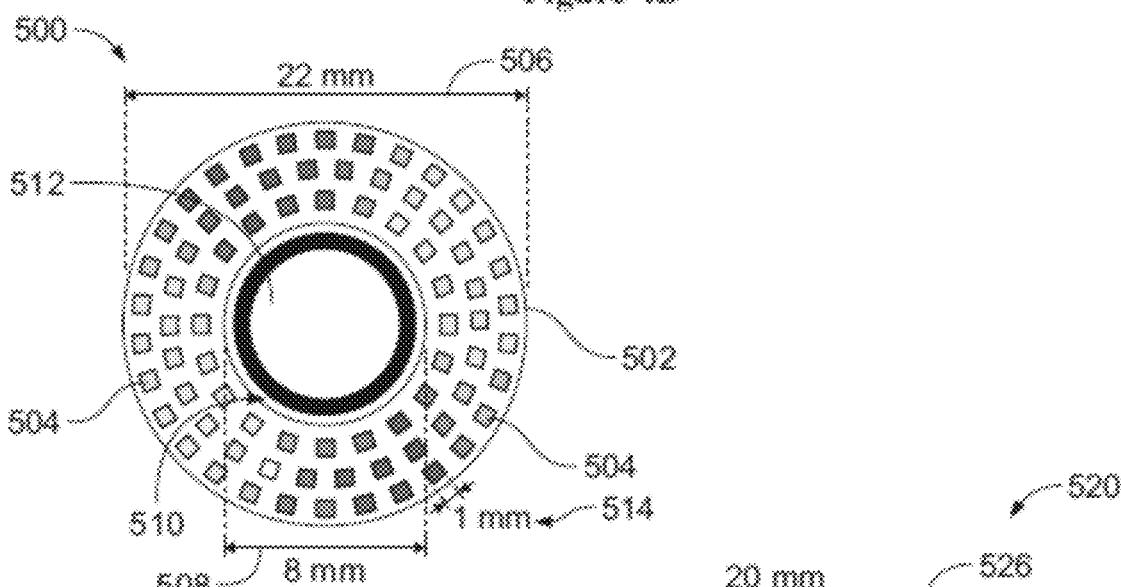
FIGS. 5A and 5B illustrate micro-LED arrays on printed circuit boards.
Figure 5B:
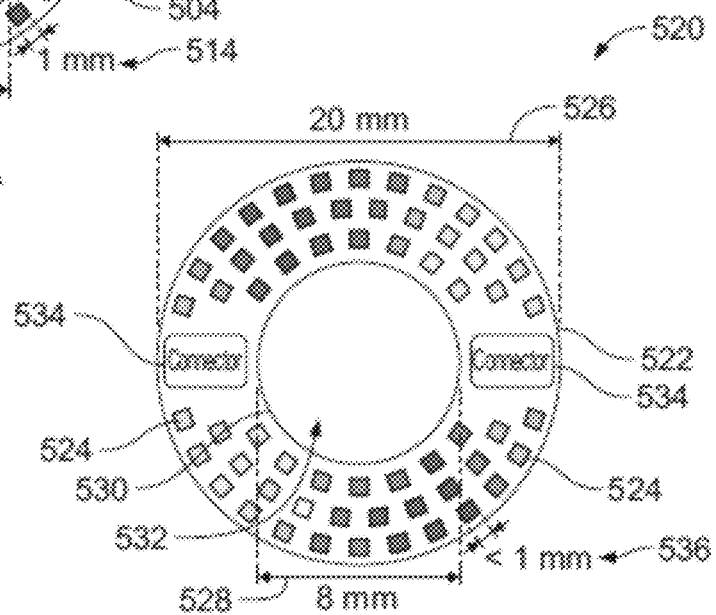

FIGS. 5A and 5B illustrate micro-LED arrays on printed circuit boards. Referring to FIG. 5A, a micro-LED array 500 on a printed circuit board (PCB) 502 includes a plurality of micro-LEDs 504. The PCB 502 can include a round, circular, or donut shape having an outer diameter 506 and an inner diameter 508. Within the inner diameter 508, an aperture 510 is provided through which a camera lens 512 of a camera is provided. In this implementation, connectors (e.g., connectors 414) can be backside connectors and the PCB 502 includes inner conductive layers.

Referring to FIG. 5B, a micro-LED array 520 on a PCB 522 includes a plurality of micro-LEDs 524. The PCB 522 can include a round, circular, or donut shape having an outer diameter 526 and an inner diameter 528. Within the inner diameter 528, an aperture 530 is provided through which a camera lens 532 of a camera is provided. The micro-LED array 520 can further include through-board connectors 534 (e.g., implementing connectors 414 of FIGS. 4A and 4B). In some cases, the connectors 534 are disposed opposite each other with respect to an axial center of the micro-LED array 520.

The positioning of the illumination sources (e.g., the plurality of micro-LEDs 504, 524) with respect to the camera or light sensor can be another important factor of an endoscopic imaging system, since the angle of reflectance and any shadowing can influence the quality of the image data produced by the system. Therefore, in some cases (e.g., as illustrated in FIGS. 5A and 5B), the micro-LEDs 504, 524 of the micro-LED array 500, 520 are positioned around a circumference of the camera or sensor, such as mounted on a PCB and surrounding the camera/camera lens 512, in order to minimize shadowing and optimize reflectance angles.

Referring to FIGS. 5A and 5B, each micro-LED 504, 524 of the micro-LED array 500, 520 can have a particular external dimension 514, 536, such as a length and width or a diameter. In some cases, the external dimension 514, 536 is equal to or less than two millimeters, equal to or less than one and a half millimeters, equal to or less than one millimeter, equal to or less than 0.9 millimeters, equal to or less than 0.8 millimeters, equal to or less than 0.7 millimeters, equal to or less than 0.6 millimeters, equal to or less than 0.5 millimeters, equal to or less than 0.4 millimeters, equal to or less than 0.3 millimeters, equal to or less than 0.2 millimeters, or equal to or less than 0.1 millimeters. In particular embodiments, the particular external dimension 514, 536 is about one millimeter. In any case, it should be understood that the particular external dimension 514, 536 can be used to determine the surface area of each micro-LED. For example, if the particular external dimension is equal to or less than two millimeters, the surface area is less than or equal to four millimeters because a length/width external dimension is length×width=2 mm×2 mm=4 mm$^2$ and a diameter external dimension is $\pi d^2/4 = 3.14 \times ((2\ mm)^2/4) = 3.14\ mm^2$. In some cases, the micro-LEDs are micro CMOS LEDs.

In various implementations, a number of the plurality of micro-LEDs 504, 524 of the micro-LED array 500, 520 is greater than or equal to ten micro-LEDs, greater than or equal to twenty micro-LEDs, greater than or equal to thirty micro-LEDs, greater than or equal to forty micro-LEDs, greater than or equal to fifty micro-LEDs, greater than or equal to sixty micro-LEDs, or greater than or equal to seventy micro-LEDs. In some cases, a number of the plurality of micro-LEDs 504, 524 of the micro-LED array 500, 520 is less than or equal to eighty micro-LEDs, less than or equal to seventy micro-LEDs, less than or equal to sixty micro-LEDs, less than or equal to fifty micro-LEDs, less than or equal to forty micro-LEDs, less than or equal to thirty micro-LEDs, or less than or equal to twenty micro-LEDs.

In some cases, the HSE system provides a spectral resolution of at least five discrete spectral bands (e.g., with each micro-LED having a discrete spectral band), such as equal to or greater than seven, equal to or greater than ten, equal to or greater than fifteen, equal to or greater than twenty, equal to or greater than twenty-five, equal to or greater than thirty, equal to or greater than thirty-five, equal to or greater than forty, equal to or greater than forty-five, or equal to or greater than fifty.

In some cases, the HSE system provides a spectral resolution of at least five complex spectral bands (e.g., a subset of the micro-LEDs that are illuminated simultaneously with varying intensities to create complex spectral bands containing multiple wavelengths of interest), such as equal to or greater than seven, equal to or greater than ten, equal to or greater than fifteen, equal to or greater than twenty, equal to or greater than twenty-five, equal to or greater than thirty, equal to or greater than thirty-five, equal to or greater than forty, equal to or greater than forty-five, or equal to or greater than fifty. In some cases, the HSE system provides a spectral resolution of discrete and complex spectral bands.

In particular embodiments, a number of the plurality of micro-LEDs 504, 524 of the micro-LED array 500, 520 is sixty micro-LEDs. At least two micro-LEDs 504, 524 of the micro-LED array 500, 520 can provide the same spectral band, such that there are thirty different spectral bands with two micro-LEDs 504, 524 of the micro-LED array 500, 520 per different spectral band. Having two micro-LEDs 504, 524 per different spectral band can decrease the occurrence of shadow artifacts in captured images. The spectral bands emitted by the micro-LED array 500, 520 can range from ultraviolet (UV) and visible spectrum (~350 nanometers to ~700 nanometers) to infrared (~700 nanometers to ~1250 nanometers). The micro-LEDs 504, 524 of the micro-LED array 500, 520 can be turned on and/or off at a certain time to provide illumination of only a particular spectral band for a particular time. Similarly, the micro-LEDs 504, 524 of the micro-LED array 500, 520 can be turned on and/or off consecutively to provide illumination of different discrete spectral bands over a range of time.

The outer diameter 506, 526 of the micro-LED array 500, 520 is equal to or less than thirty millimeters. For example, the outer diameter 506, 526 of the micro-LED array 500, 520 can be equal to or less than twenty-eight millimeters, equal to or less than twenty-six millimeters, equal to or less than twenty-four millimeters, equal to or less than twenty-two millimeters, equal to or less than twenty millimeters, equal to or less than eighteen millimeters, equal to or less than sixteen millimeters, equal to or less than fourteen millimeters, equal to or less than twelve millimeters, or equal to or less than ten millimeters. In some cases, the outer diameter 506, 526 of the micro-LED array 500, 520 is greater than or equal to eight millimeters. For example, the outer diameter 506, 526 of the micro-LED array 500, 520 can be greater than or equal to ten millimeters, greater than or equal to twelve millimeters, greater than or equal to fourteen millimeters, greater than or equal to sixteen millimeters, greater than or equal to eighteen millimeters, greater than or equal to twenty millimeters, greater than or equal to twenty-two millimeters, or greater than or equal to twenty-four millimeters. In particular embodiments, the outer diameter 506, 526 of the micro-LED array 500, 520 is about twenty millimeters or about twenty-two millimeters.

The inner diameter 508, 528 of the micro-LED array 500, 520 is greater than or equal to two millimeters. For example, the inner diameter 508, 528 of the micro-LED array 500, 520 can be greater than or equal to four millimeters, greater than or equal to six millimeters, greater than or equal to eight millimeters, greater than or equal to ten millimeters, or greater than or equal to twelve millimeters. The inner diameter 508, 528 of the micro-LED array 500, 520 is less than or equal to fourteen millimeters. For example, the inner diameter 508, 528 of the micro-LED array 500, 520 can be less than or equal to twelve millimeters, less than or equal to ten millimeters, less than or equal to eight millimeters, less than or equal to six millimeters, or less than or equal to four millimeters. In particular embodiments, the inner diameter 508, 528 of the micro-LED array 500, 520 is about eight millimeters.

Figure 6A:
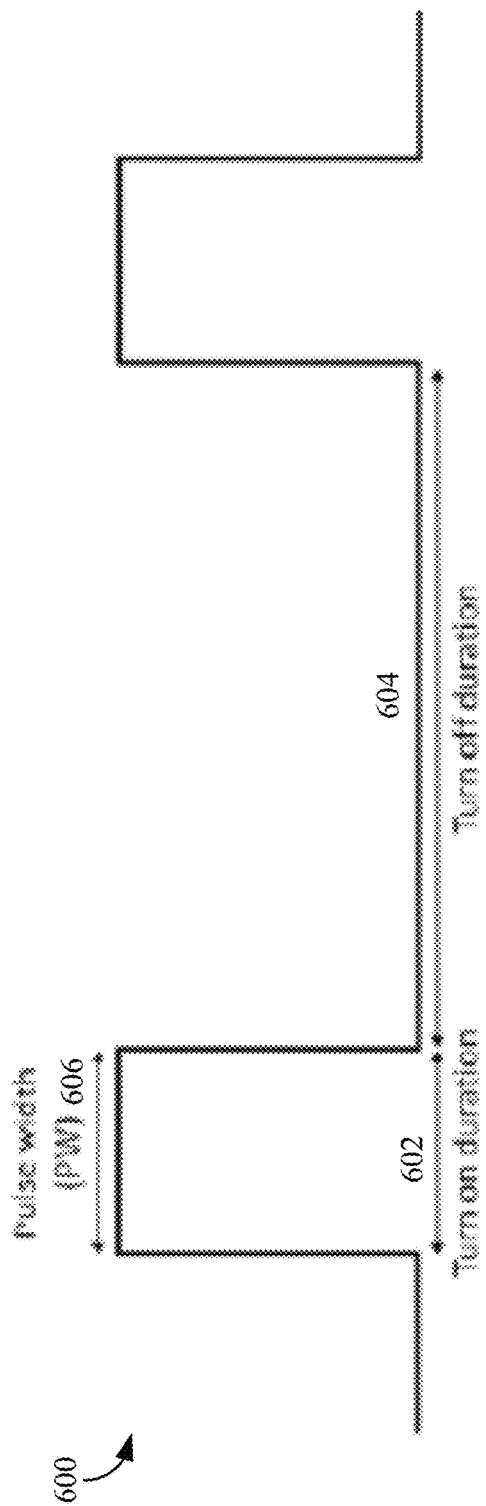
Figure 6B:
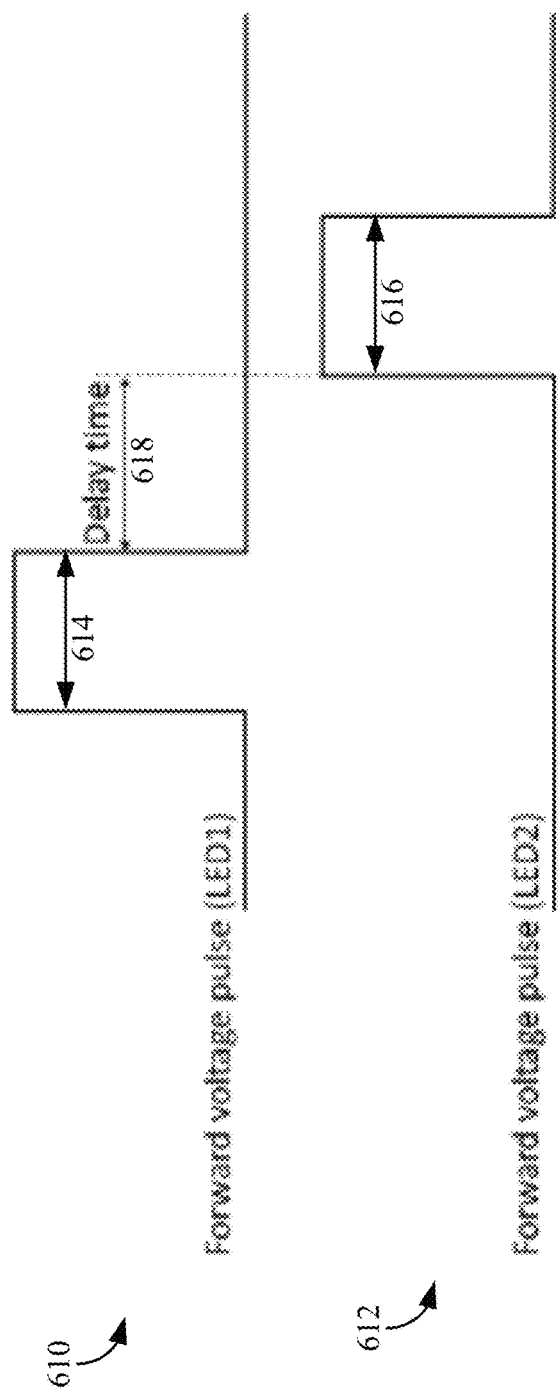

FIGS. 6A-6C illustrate forward pulse signals sent to a micro-LED array. Referring to FIG. 6A, a timing signal 600 includes a turn on duration 602 and a turn off duration 604 that can be controlled by a pulse width 606 sent to a micro-LED of a micro-LED array. A variable that directly affects an imaging frame rate of an HSE system is each LEDs turn on delay. Turn on delay includes the time it takes for a micro-LED to achieve its highest illumination level (which is the optimal lighting condition to capture an image) after receiving a turn on signal. Therefore, an optimal pulse width for each micro-LED is needed. For the example implementations, to determine an optimal pulse width 606 for each micro-LED of the micro-LED array, the signal-to noise ratio (SNR) of each captured image in the ROI was measured first. To measure the SNR of each captured image in the ROI, square-shaped forward biased signal pulses with different pulse widths were sent to one micro-LED using an FGPA and an image per pulse was captured. For each captured image, SNR was calculated at the ROI of the image using the formula:

$$SNR_{dB} = 20\log_{10}\left(\frac{\mu_{ROI}}{\sigma_{ROI}}\right),$$

where $\mu_{ROI}$ is the average reflectance of the ROI and $\sigma_{ROI}$ is the standard deviation of the ROI.

Referring to FIG. 6B, a timing diagram is shown for a first timing signal 610 for a first micro-LED and a second timing signal 612 for a second micro-LED. The first timing signal 610 shows a pulse with a first LED pulse width 614. The second timing signal 612 shows a pulse with a second LED pulse width 616. A time delay 618 is shown between the first timing signal 610 and the second timing signal 612. Illumination interference between illumination of a first micro-LED (corresponding to the first timing signal 610) and illumination of a second micro-LED (corresponding to the second timing signal 612) can occur in a ROI if the time delay 618 is not sufficient. Therefore, a time delay 618 can be optimized for minimum time and minimum interference between illuminations of micro-LEDs by determining the turn on delay (e.g., as described with respect to FIG. 6A) and determining a minimal illumination interference that can be achieved for quality real-time or rapid imaging.

In example implementations, to determine the minimal illumination interference that can be achieved for quality real-time or rapid imaging, a time delay 618 between an image taken using a reflection spectral band of a first micro-LED for a ROI (ROI$_1$) and an image taken using a reflection spectral band of a second micro-LED for the ROI (ROI$_2$) was changed (e.g., reduced and/or increased) until the minimal illumination interference was found. Specifically, measuring the proportion of the ROI$_1$ reflection to the ROI$_2$, reflection on the first captured image (I$_1$) and the proportion of the ROI$_2$ reflection to the ROI$_1$ reflection on the second captured image (I$_2$) using varying time delays 618 between capturing the first and second image allowed the inventors to determine an average of both proportional values of the captured images, hereinafter referred to as the interference factor (IF), which can be used to determine an overlap between illuminations of the micro-LEDs. The IF illustrates interference between the captured images and impacts the spectral resolution of the HSE system. Therefore, by measuring the IF with varying time delays 618, the minimum time interval with minimum interference between the captured images is determined. The IF can be determined using the formula provided below:

$$F = 2\left[\frac{1}{N_1}\sum_{x \in ROI_1} I_1(x) / \frac{1}{N_2}\sum_{x \in ROI_2} I_1(x)\right] + \left(\frac{1}{N_2}\sum_{x \in ROI_2} I_2(x) / \frac{1}{N_1}\sum_{x \in ROI_1} I_2(x)\right)\right]^{-1},$$

where $N_1$ and $N_2$ are the number of pixels of ROI$_1$ and ROI$_2$, respectively.

Referring to FIG. 6C, a timing diagram 620 is shown for illuminations of thirty micro-LEDs. By determining IF for images captured using micro-LEDs having thirty discrete spectral bands (e.g., with an image captured for each discrete spectral band), a time delay between timing signals for each micro-LED can be optimized for minimum time and minimum interference between illuminations of micro-LEDs. In some cases, the pulse width of each timing signal is equal to or less than ten milliseconds. In some cases, each timing signal is equal to or less than eight milliseconds, equal to or less than six milliseconds, equal to or less than four milliseconds, or equal to or less than two milliseconds.

Figure 7:
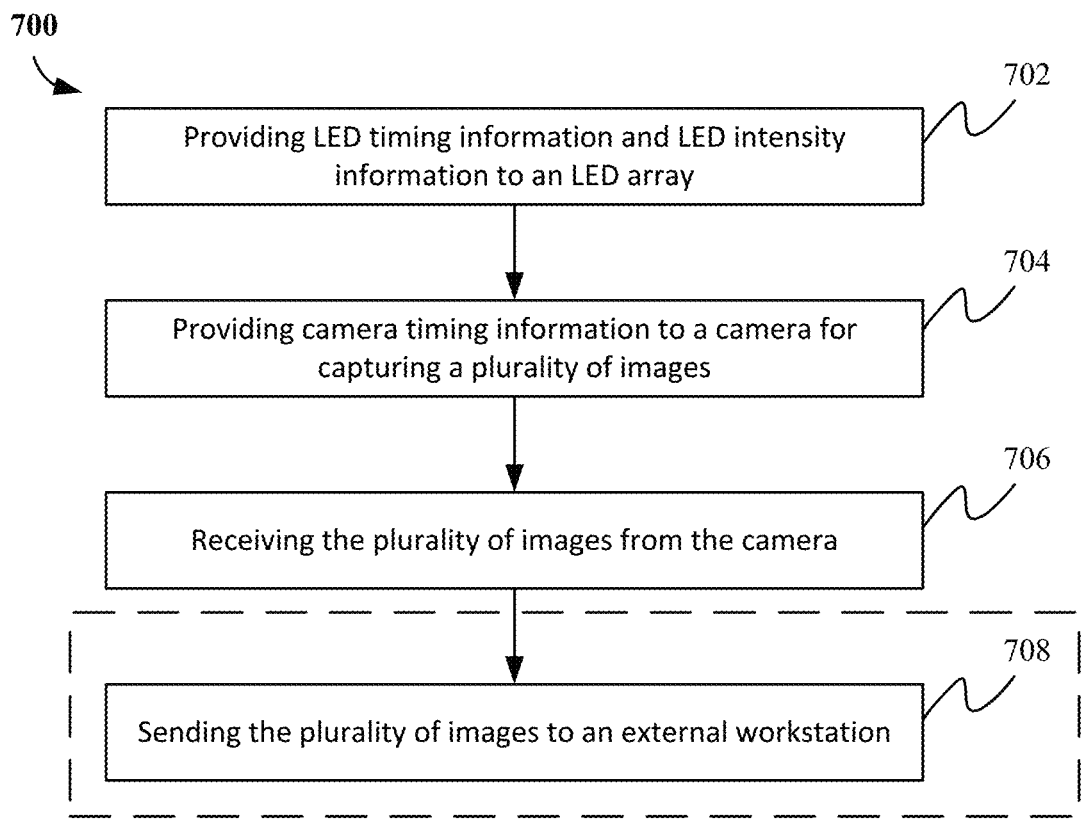
FIG. 7 illustrates a method of controlling a hyperspectral imaging device.

FIG. 7 illustrates a method of controlling a hyperspectral imaging device. Referring to FIG. 7, the method 700 includes providing (702) LED timing information and LED intensity information to a micro-LED array. The micro-LED array includes micro-LEDs of varying spectral bands. The timing information includes a timing signal to each LED of the LED array with each timing signal including a pulse. For example, an imaging controller can simultaneously send a turn on signal (e.g., a pulse) to illuminate one or more micro-LEDs (e.g., with a turn on signal being sent for each micro-LED) having a discrete spectral band and/or include simultaneously sending a turn on signal to each micro-LED of a subset of micro-LEDs to illuminate the subset of the micro-LEDs (with the subset of micro-LEDs including micro-LEDs with varying spectral bands) that creates a complex spectral band. In some cases, the timing signal also includes a turn off signal that is sent to the micro-LEDs that received the turn on signal; in some cases, the turn on signal simply ends (resulting in the corresponding micro-LEDs turning off).

The method 700 further includes providing (704) camera timing information to a camera for capturing a plurality of images. An image of the plurality of images is captured for a time period associated with each timing signal. For example, when one or more micro-LEDs simultaneously receive a turn on signal to illuminate, camera timing information sent from the imaging controller causes the camera to capture an image (e.g., after the turn on delay so the one or more micro-LEDs have achieved their highest illumination level). After the time delay, when one or more different micro-LEDs simultaneously receive a turn on signal to illuminate, the camera timing information sent from the imaging controller causes the camera to capture another image (e.g., after the turn on delay so the one or more different micro-LEDs have achieved their highest illumination level). The camera timing information causes the camera to capture an image for a time period associated with each illumination of micro-LEDs for all spectral bands that are emitted.

Operations 702 and 704 can be performed continuously (and simultaneously) until micro-LEDs for all spectral bands (e.g., discrete and/or complex spectral bands) that are needed for the particular test to identify one or more tissues and/or all available spectral bands (e.g., discrete and/or complex spectral bands) have received a turn on signal. For example, after pausing for a time delay that is optimized for minimum time and minimum interference between illuminations of micro-LEDs, the imaging controller can simultaneously send a turn on signal to illuminate one or more micro-LEDs (e.g., with a turn on signal being sent for each micro-LED) having a different discrete spectral band and/or include simultaneously sending a turn on signal to each micro-LED of a subset of micro-LEDs to illuminate the subset of the micro-LEDs (with the subset of micro-LEDs including micro-LEDs with varying spectral bands) that creates a different complex spectral band. In addition, the imaging controller can send camera timing information to the camera to capture images for these next selected micro-LEDs. This process repeats (e.g., a time delay followed by a turn on signal(s)) until micro-LEDs for all spectral bands (e.g., discrete and/or complex spectral bands) that are needed for the particular test to identify one or more tissues and/or all available spectral bands (e.g., discrete and/or complex spectral bands) have received a turn on signal.

The method 700 further includes receiving (706) the plurality of images from the camera. In some cases, the method 700 further includes sending (708), via a transceiver, the plurality of images to an external workstation. In some cases, the imaging controller can receive (706) and send (708) a single image of the plurality of images at a time. In some cases, the imaging controller can receive (706) and/or send (708) a first set of the plurality of images at a time, wherein the first set of the plurality of images includes an image for each for all spectral bands that have been illuminated. For example, a first set of images can be taken of a particular tissue of a patient followed by a second set of images of a different particular tissue of the patient; the first set of images can be sent as a package to the external workstation followed by the second set of images. In some cases, each image in a set of images can be received one at a time.

In some cases, the imaging controller (e.g., imaging controller 108 of FIG. 1 and/or imaging controller 208 of FIG. 2) includes instructions stored within memory that are performed by a processor to provide LED timing information and LED intensity information to a micro-LED array and/or provide camera timing information to a camera. Alternatively, or in addition, the functionality for providing LED timing information and LED intensity information to a micro-LED array and/or providing camera timing information to a camera can be performed, at least in part, by one or more hardware logic components of the HSI system. For example, and without limitation, illustrative types of hardware logic components that can be used include microcontrollers, field-programmable gate arrays (FPGAs), application-specific integrated circuits (ASICs), application-specific standard products (ASSPs), system-on-a-chip systems (SOCs), complex programmable logic devices (CPLDs), etc.

In some cases, an external workstation/computer includes an image processor to produce an image from the light image data. The image processor can include a central processing unit (CPU), a graphics processing unit (GPU), an application specific processor, or logic devices, as well as any other type of processing device, combinations, or variations thereof that execute software and/or perform logic operations to produce an image for display. The image processor may use the light image data to produce an image on a display connected to the external workstation/computer.

The imaging controller and/or external workstation may also include one or more storage resources including storage (e.g., to store the light image data and/or captured images). The one or more storage resources can include volatile and non-volatile memories, removable and non-removable media implemented in any method or technology for storage of information, such as computer readable instructions, data structures, program modules, or other data. Examples of storage resources include storage devices in the form of random access memory, read only memory, magnetic disks, optical disks, CDs, DVDs, flash memory, magnetic cassettes, magnetic tape, magnetic disk storage or other magnetic storage devices, or any other suitable storage media. In no case is a storage resource implementing the storage a transitory propagated signal. Indeed, as used herein "storage media" do not consist of transitory, propagating waves. Instead, "storage media" refers to non-transitory media. Storage can store instructions for the processes carried out by the HSI system, including instructions for providing LED timing information and LED intensity information to a micro-LED array and/or providing camera timing information to a camera, receiving of a plurality of image and sending the plurality of images to an external workstation. It is further contemplated that said instructions can be stored at any suitable computer-readable storage medium for execution by any imaging system. Again, it should be understood that "computer-readable storage medium" does not consist of transitory propagating signals.

In some cases, the external workstation may be remote from the HSE device (e.g., on-site, off-site, or cloud-based) to securely receive the plurality of images from the imaging controller. In some cases, communications interfaces for sending/receiving the plurality of images can include a network interface for coupling to the Internet or cellular service (e.g., for communicating with a service tied to a mobile application on a mobile device) and/or a short-range interface (near field, wide band, Bluetooth®, or other common communication protocols) that can be used to communicate wirelessly with nearby devices. In some cases, the communications interfaces can include direct interfaces for particular sensors or general interfaces such as USB, Ethernet, or FireWire.

EXPERIMENTS

The inventors set up experiments using an HSE device, such as described with respect to FIG. 2, inside of a dark box (e.g., to simulate the inside of a patient's body), with the resulting images being transmitted to an external workstation for image processing. Specifically, the camera is model UC10MPC_L36 camera manufactured by Spinel (Orange County, CA), which is a CMOS monochrome camera with 3.6 mm lens and FOV of 90°. The image sensor size is ¼ inches with 1280×720 pixels. The physical pixel size is 3 μm. The camera has no optical filter. The maximum imaging frame rate of the camera is 120 fps. The processing and controlling module used was a Xilinx Kintex 7 FPGA on a Genesys 2 evaluation board from Agilent. The LED array includes through-hole LEDs from Marubeni Corporation (Tokyo, Japan). Seven LEDs of discrete spectral bands of were tested, including 405 nm, 505 nm, 555 nm, 610 nm, 660 nm, 700 nm, and 740 nm. Table 1 shows the specifications of each LED used in these experiments.

TABLE 1

The specifications of the LEDs used in the experiments

| Peak Wavelength (nm) | 405 | 505 | 555 | 610 | 660 | 700 | 740 |
|---|---|---|---|---|---|---|---|
| Half Width (nm) | 19 | 30 | 25 | 15 | 18 | 21 | 24 |
| Typical Viewing Angle (degrees) | 102 | 86 | 40 | 30 | 80 | 80 | 20 |

Figure 8A:
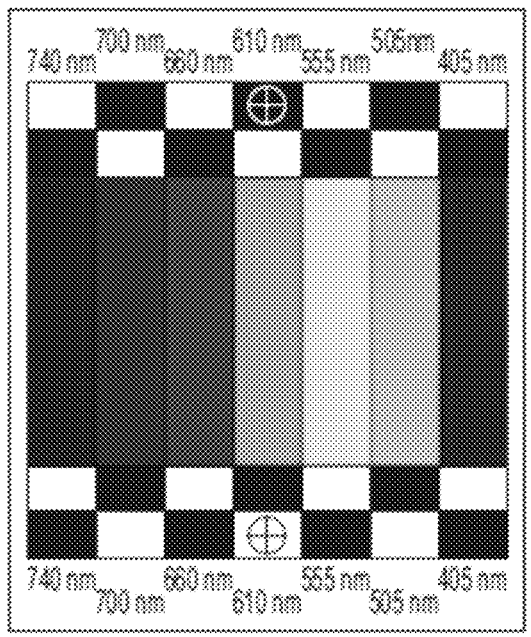
FIG. 8A illustrates an electronic version of a simple hyperspectral evaluation template.
Figure 8B:
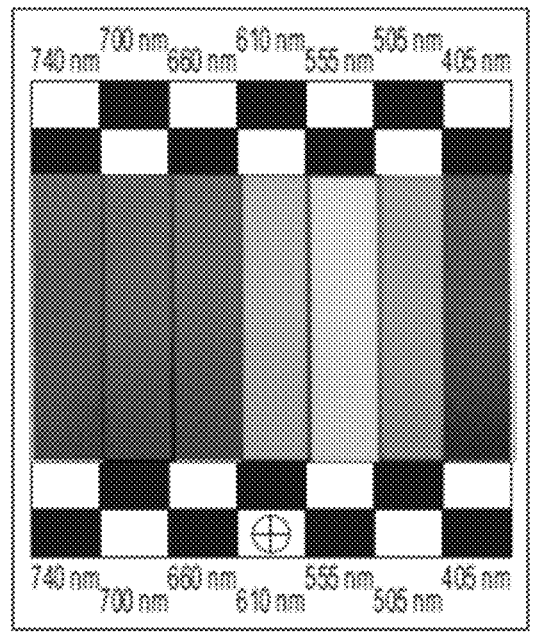
FIG. 8B illustrates a printed version of the simple hyperspectral evaluation template that was printed and positioned inside the dark box.

FIG. 8A illustrates an electronic version of a simple hyperspectral evaluation template. FIG. 8B illustrates a printed version of the simple hyperspectral evaluation template that was printed and positioned inside the dark box. The size of the evaluation template was 50 mm×50 mm and it had seven 7 mm×30 mm bars each corresponded to one wavelength, as well as black and white sections and focusing markers. After printing the template, it was coated with an anti-reflective material for glare reduction during imaging. This was done in order to characterize the system. As can be seen, the colors in FIG. 8B are slightly different than the colors in FIG. 8A, which is ascribed to limitations of the printer used for printing. This color shift may account for certain error in results.

The following experiments were performed to evaluate certain factors that may influence imaging quality of the system, and particularly the LED array and its impact on the imaging parameters such as imaging rate and noise level. The camera, the template, and the LED array were then placed inside the dark box to block the environment light during the experiments. The camera lens was optically shielded by a lens hood to avoid any direct illumination from LEDs. The LEDs were turned on and off by the FPGA evaluation board.

Experiment I (Turn on Delay)

The turn on delay experiment helps to define the optimum PW for turning on the LEDs in the imaging system. The signal-to-noise ratio (SNR) of the captured images in the region of interest (ROI) was measured as follows: square-shape signal pulses with different pulse widths (PWs) were sent to one LED and a snapshot per pulse was recorded. In particular, the inventors forward biased an LED using pulse waves with different pulse widths (PWs) and recorded a snapshot per pulse wave. For generating and applying the pulses with different PWs the inventors used the FPGA. For each image, the inventors calculated the SNR at the corresponding region (the ROI correspond to the illumination spectral band) on the image. Each ROI occupied about 70×305 pixels. Here, the inventors measured the SNR using the average reflectance of the ROI ($\mu_{ROI}$) divided by its standard deviation ($\sigma_{ROI}$):

$$SNR_{dB} = 20\log_{10}\left(\frac{\mu_{ROI}}{\sigma_{ROI}}\right).$$

Figure 9:
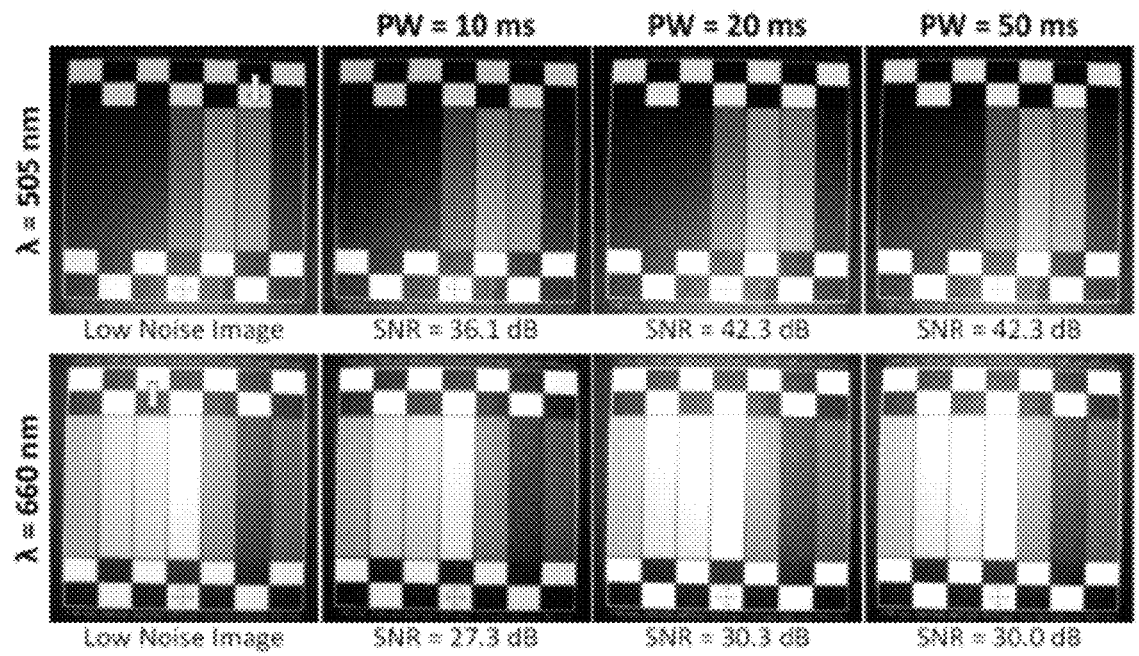
FIG. 9 illustrates images captured of the printed version of the simple hyperspectral evaluation template.
Figure 10:
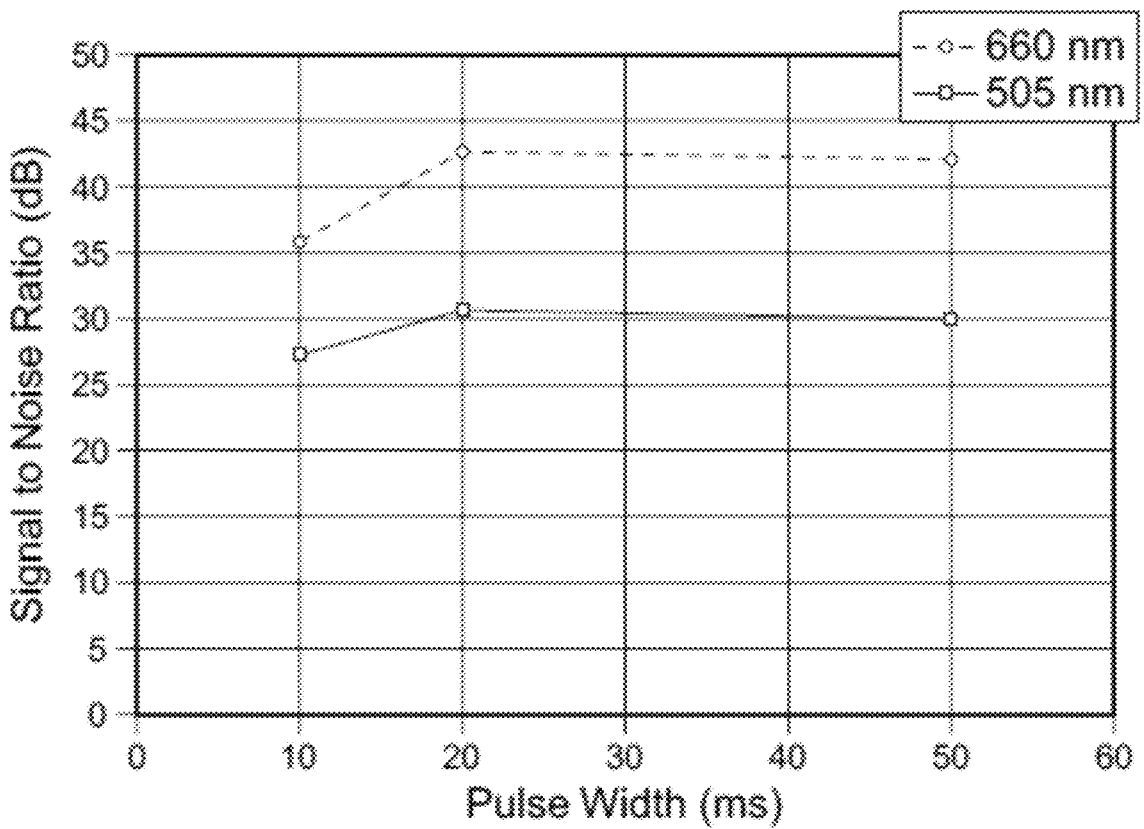
FIG. 10 illustrates the SNRDB based on the pulse width.

The inventors repeated this experiment twice using two LEDs with spectral bands of 505 nm and 660 nm. FIG. 9 illustrates images captured of the printed version of the simple hyperspectral evaluation template that was printed and positioned inside the dark box when different PWs were applied to the LEDs. The top row images were captured when the pulses were applied to the LED with a peak spectral band of 505 nm and the bottom row images were captured when the pulses were applied to the LED with a peak spectral band of 660 nm. To generate low noise images, the inventors also applied a DC forward voltage to each LED and captured several frames. By using an averaging filter across the captured frames, a low noise image per spectral band can be generated as a reference image. The first images from the left on each row show the low noise images for the corresponding LEDs. FIG. 10 illustrates the SNRDB based on the pulse width.

Experiment II (Sensitivity of the Image Quality to the Forward Voltage of the LED)

Since the driving voltage of the LED can control its illumination, and the typical driving voltage (forward voltage) for LEDs are different, it can be helpful to investigate the sensitivity of the LED illumination and image quality to the forward voltage. The results of this experiment can be helpful in determining effective driving of the LED array. In this experiment, the inventors quantify the quality of the images using SNR and reflection. Here, reflection can be defined as the percentage of the light returned from the corresponding ROI on the evaluation template to the camera.

Figure 11A:
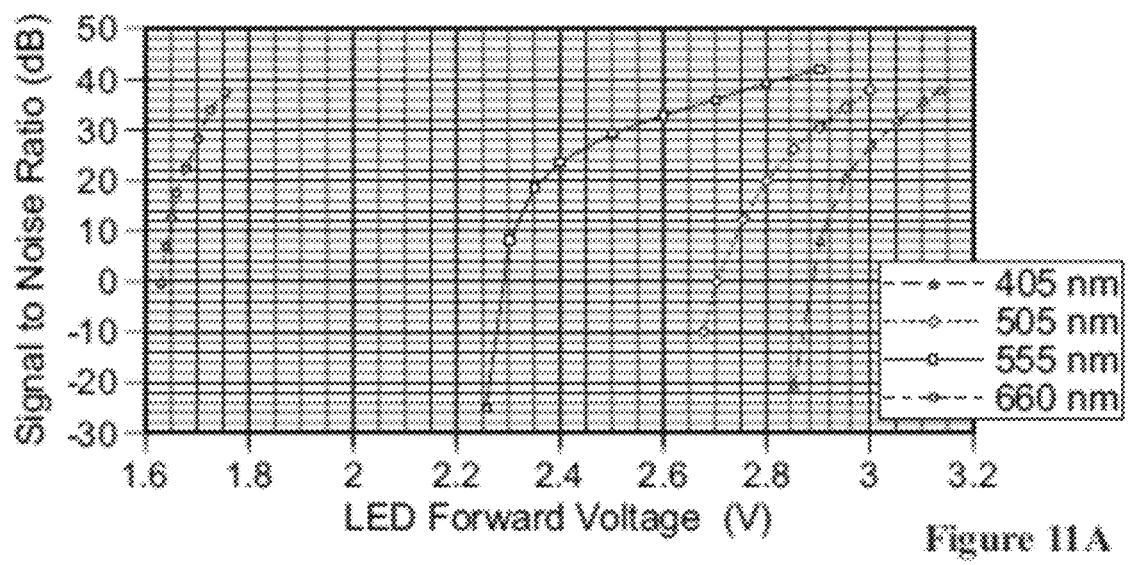
FIG. 11A illustrates the SNRDB of the captured images based on the forward voltage applied to the micro-LED.
Figure 11B:
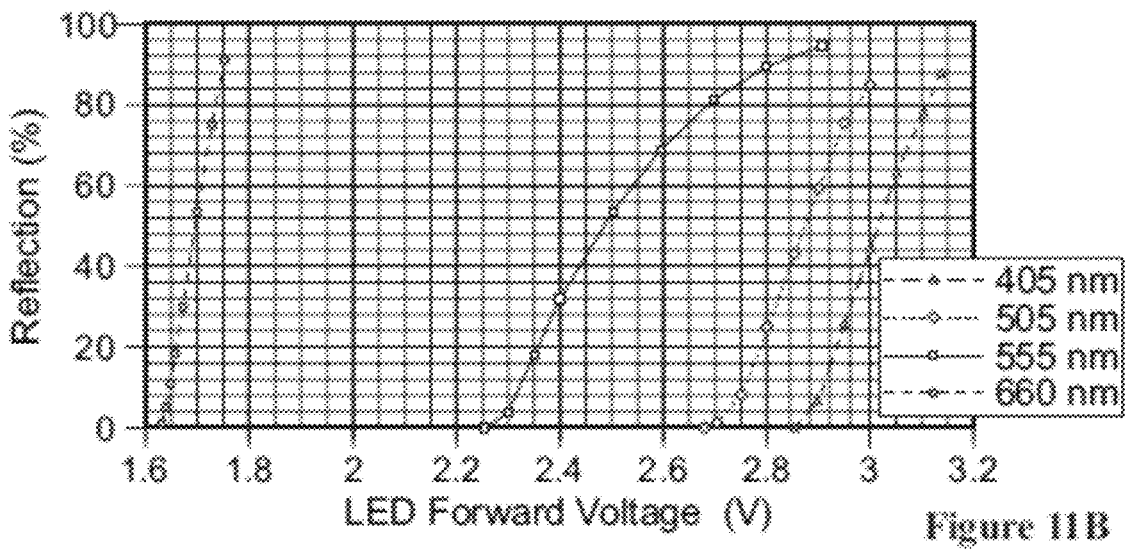
FIG. 11B illustrates the percentage of the reflected light from the corresponding ROI for each micro-LED.

The inventors turned on each LED using different forward voltages. The inventors put a potentiometer in series with LEDs to control its illumination by changing its forward voltage. Then, for each adjusted voltage, the inventors captured an image and calculated the $SNR_{dB}$ and the percentage of the reflected light from the corresponding ROI. The inventors repeated this experiment using LEDs with peak spectral bands of 405 nm, 505 nm, 555 nm, and 660 nm. FIG. 11A illustrates the $SNR_{DB}$ of the captured images based on the forward voltage applied to the LED. FIG. 11B illustrates the percentage of the reflected light from the corresponding ROI for each LED.

Experiment III (Spectral Resolution)

In this experiment, the inventors quantify the potential illumination interference between two LEDs that were switched on and off one after the other with a delay in between. The LEDs are controlled with pulse waves applied to their anode as a forward bias voltage. The inventors turned on and off two LEDs with two different spectral bands one after the other and captured two snapshots. The inventors evaluate the imaging quality using the two corresponding ROIs on the evaluation template. One ROI used the reflection spectral band of the first LED ($ROI_1$) and the other with the reflection spectral band of the second LED ($ROI_2$). The inventors reduced the time delay between turning off the first LED and turning on the second one and measured the proportion of the $ROI_1$ reflection to the $ROI_2$ reflection on the first snapshot ($I_1$) and the proportion of the $ROI_2$ reflection to the $ROI_1$ reflection on the second snapshot ($I_2$). The inventors get the average of both proportional values (e.g., the IF) as a metric for investigating the overlap between the illuminations of the two LEDs. The IF shows the interference between the two snapshots and has an impact on the spectral resolution of the HSE imaging system. The inventors measure the IF at different time intervals to find the minimum time interval with minimum interference between the two snapshots. The equation used for the IF is described above.

Figure 12:
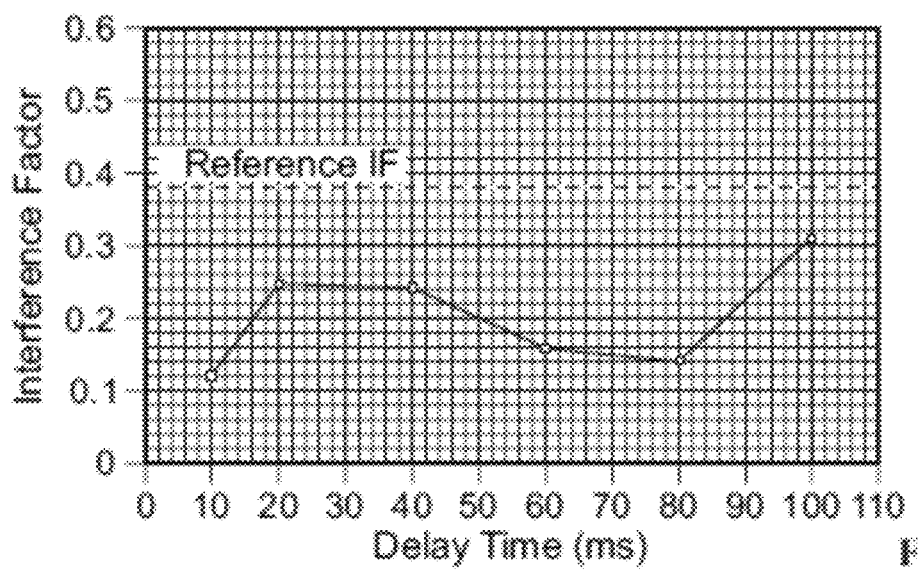
FIG. 12 illustrates the IF values for the two micro-LEDs versus time delay.

The inventors shifted the pulse wave applied to one LED for generating the appropriate pulse for driving the other LED. By changing the amount of phase shift between these two pulses the inventors determine the delay between turning off an LED and turning on the other one. The inventors measured IF to assess the illumination interference between the two LEDs. The inventors conducted this experiment using an LED pair with peak spectral bands of 505 nm and 660 nm. As a reference, the inventors measured the IF when no interference can be involved using the two low noise images obtained in Experiment I. The measured reference IF was 0.38. Any IF value above this could be interpreted as illumination interference between the two LEDs. FIG. 12 illustrates the IF values for the two LEDs versus time delay. The reference IF value can be shown as a horizontal dashed line on the graph.

Experiment IV (Multispectral or Hyperspectral Imaging)

In this experiment, the inventors turned on and off all the seven LEDs in sequence to evaluate the quality of the datacube. The inventors measured the SNR of the one datacube and the SNR of each channel at its corresponding ROI. This experiment is illustrative of the feasibility of HSE using LED-array for illumination.

Figure 13:
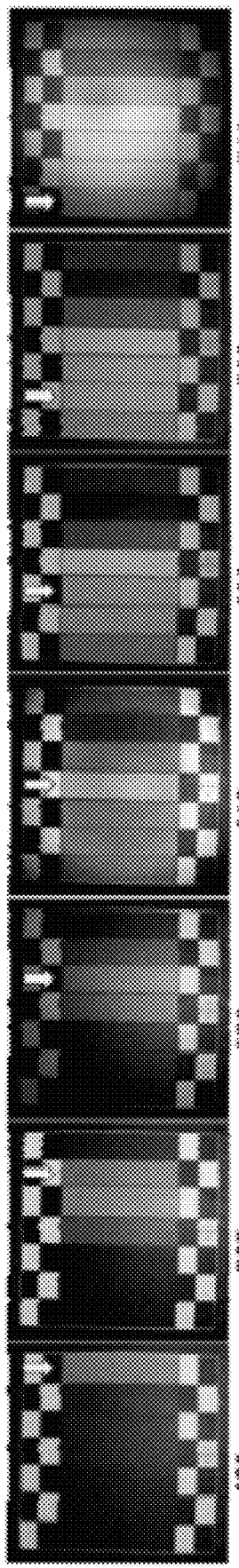
FIG. 13 illustrates the seven channels of the data cube.

The inventors set the PW and delay time both to 10 milliseconds and manually optimized the forward voltages of the LEDS to obtain a similar reflectance for all the seven bands, roughly speaking. FIG. 13 illustrates the seven channels of a datacube. The $SNR_{dB}$ of the datacube was 18.9 dB. The $SNR_{dB}$ values for the seven channels at the corresponding ROIs were 27.6 dB, 27.2 dB, 25.3 dB, 32.2 dB, 27.7 dB, 28.3 dB, and 22.7 dB for 405 nm, 505 nm, 555 nm, 610 nm, 660 nm, 700 nm, and 740 nm, respectively. The inventors achieved a seven-channel multispectral imaging rate of about 7.2 fps using the proposed approach with a monochrome camera with 120 fps imaging rate.

The main features of an HSE system are spatial resolution, spectral resolution, FOV, and imaging frame rate. The results of the experiments described above are illustrative that using a multispectral LED array combined with a monochrome camera is effective for a high-resolution and high-speed spectral band (or wavelength) scanning HSE imaging. FIG. 10 illustrates that reducing the LED lighting duration (forward voltage PW) to 10 ms slightly decreased the SNR, but it was still high enough for a high-quality imaging. A comparison between the low noise images and the captured images in FIG. 9 supports this observation. For these experiments, the maximum imaging rate of the camera (120 fps) was a bottleneck for testing shorter PWs. However, it can be estimated by extrapolation of the SNR data that this approach can be used confidently for imaging with forward voltage PWs as short as few milliseconds. In addition, the results of Experiment III show that reducing the time delay did not cause illumination interference and the LEDs could be switched with time gaps shorter than 10 ms. Hence, assuming a 2 ms PW and time delay, a frame rate of 250 fps is possible. That means with 10 spectral bands, the HSE system can generate 25 multispectral images per second, which can be considered real-time imaging. If the HSE system includes 20 spectral bands, the HSE system can achieve 12 multispectral images per second, which can be rapid imaging. Use of a higher-speed camera can improve over the estimations provided above.

The results of Experiment II show that the level of the LED forward voltage plays an important role in the quality of the images. The different behavior of the LEDs suggests optimizing the voltage level for each LED separately. Besides, the viewing angle of the LEDs had a high impact on the quality of the images. For peak spectral bands 555 nm, 610 nm, and 740 nm; the inventors see a high inhomogeneity of the intensity on the images (specifically at the corners of the images) in FIG. 13. This inhomogeneity was higher for 740 nm with the narrowest viewing angle (20°) shown in Table 1. This suggests using LEDs with wider viewing angle (e.g., higher than 60°) to avoid imaging artifacts caused by inhomogeneous illuminating of the imaged tissue.

In the experiments above, the FOV was about 50 mm×50 mm and the image size was 512×512 pixels. Therefore, pixel size was about 0.098 mm. This FOV and spatial resolution for this HSE system can meet or exceed requirements for typical endoscopic systems. The seven-channel multispectral imaging rate of 7.2 fps with a monochrome camera with imaging rate of 120 fps illustrates that embodiments of the current invention could be used for a high-speed endoscopic imaging, especially those embodiments employing camera having a faster imaging rate than 120 fps. Still, embodiments of the current invention providing SNR IB values greater than 20 dB show that the quality of the imaging can be high. Embodiments providing real-time multispectral or hyperspectral imaging with more than 20 spectral channels may require a camera with at least 500 fps, depending on other components and limitations of the system. Further, embodiments having micro-LEDs may provide superior results, accompanied by appropriate setup with respect to incident angle of the LED array.

It will be appreciated that the limited space available for small endoscopes of the present invention may restrict the number of micro-LEDs at a particular size that could be used in the micro-LED array light source and, therefore, the number of spectral channels capable by such an embodiment. It will also be appreciated that the wireless connection can become a bottleneck at higher imaging speeds, and can be influenced by endoscope size, power system (e.g., battery size and capacity), etc. Thus, an appropriate wireless system and corresponding components should be chosen accordingly.

Embodiment Example for Real-Time Hyperspectral Endoscopic Imaging Using 30 LEDs

A system in accordance with an embodiment for providing a real-time HSE imaging system using 30 LEDs can include the following sub-systems:

1) LED Array with spectral bands ranging from 355 nm to 1450 nm and about 200 μm*200 μm to 400 μm*400 μm.

2) Processing and Controlling Component with FPGA/ASIC including a data calibrator, an imaging controller with a pulse generator and clock distributor.

3) Wireless transceiver with broadcam and single band capabilities, 2.4 GHz frequency band, IEEE 802.11 b/g/n, PHY layer rates of up to 300 Mbs, and a FCFBGA package 10 mm×10 mm, 0.4 mm pitch.

4) Camera Component includes a camera from Omnivision Company that provides both commercial and customized cameras. A commercial camera provides 480 fps at QVGA quality (320*240). For the HSE system, the inventors customized the camera with lower resolution and higher frame rate (600 fps). The optical format and the size of the lens are 0.1 inch (2.54 mm).

5) Software Control Component (e.g., included in the external workstation) that includes image denoising, image channel integration, and image classification.

The duration of one hyperspectral frame ($t_{HSI}$) for a system having 30 LEDs can be described as: 30(PW+DT).

The hyperspectral frame rate can thus be described as:

$$FR_{HS} = \frac{1}{t_{HSI}}.$$

For a hyperspectral frame rate of 20 fps, $t_{HSI}$ must be 50 ms. Therefore: PW+DT≈1.67 ms.

Supposing PW=DT: PW=DT≈860 μs.

Figure 14:
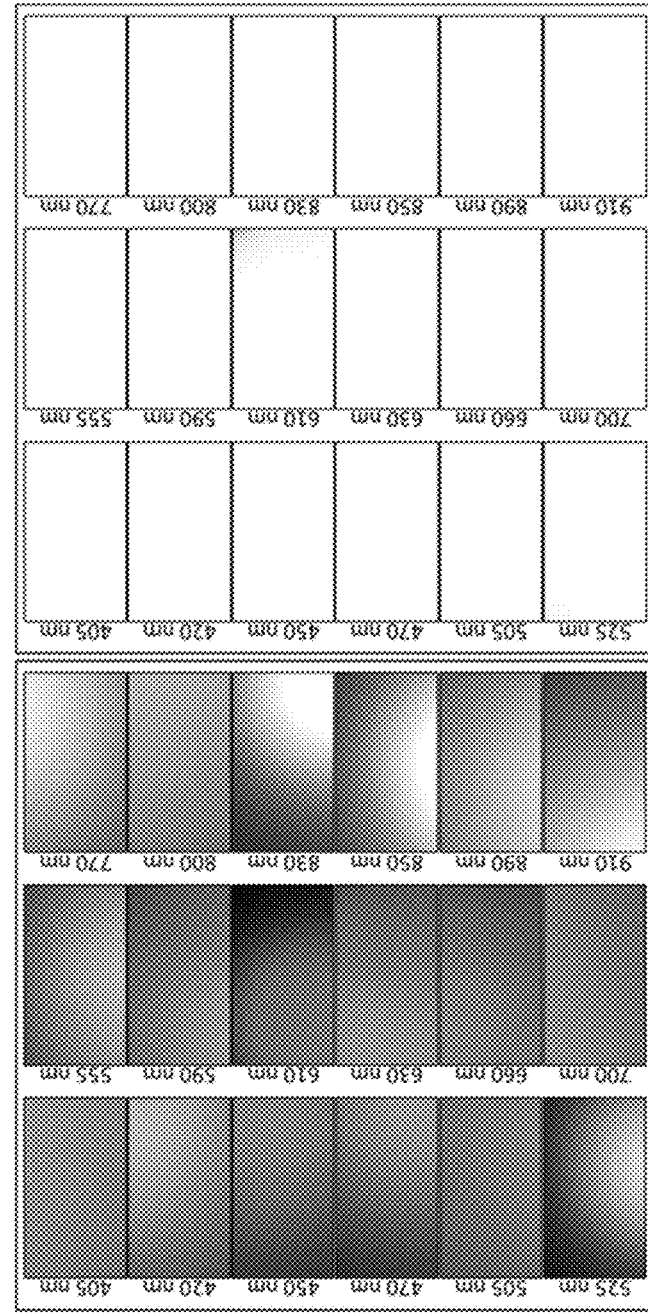
FIG. 14 illustrates captured images utilizing the HSE device from a template before and after calibration.

The switching time (rise time+fall time) of the LEDs is in the order of nanoseconds. FIG. 10 confirms that the switching times of the LEDs are less than 200 ns. Therefore, there is no interference between LEDs for an embodiment including 30 LEDs. FIG. 14 is a schematic diagram illustrating connections between a control and processing module, multiplexer, and 30 LEDs for real-time multispectral/hyperspectral endoscopic imaging, in accordance with an embodiment.

Calibration of an HSE System:

Calibration of an HSE system according to one or more embodiments can include a general spatial and spectral calibration. It will be appreciated that the LEDs' illumination power and the sensitivity of camera sensor elements can be variable. Therefore, an image intensity calibration may be required to adjust the intensity of the spectral images and to compensate the spatial and spectral inhomogeneity in LEDs' illuminations and the spatial inhomogeneity in camera sensors. For calibration, it is preferable to ensure that there is no intensity recorded when there is no light (e.g., black) and the intensity is at the highest level (e.g., white) when the LEDs are on. To adjust the images at no illumination, the endoscope tip can be covered to block all the lights and keep all the LEDs off. Camera images can then be recorded for N=100 frames. In an embodiment having 30 LEDs, for example, using a pixel-wise averaging across all the 100 images, the inventors have one 2D, low-noise image (B) that is expected to be completely black (zero intensity). Any offset on B elements must be cancelled out during calibration. To adjust the offsets, B is subtracted from each spectral image:

$$\forall i \in \{1, 2, \ldots, N\} : \hat{H}_b(i) = H(i) - B,$$

where i is the spectrum number, N is the number of spectral bands, H(i) is the $i^{th}$ hyperspectral image before no-illumination calibration, and $\hat{H}_b(i)$ is the $i^{th}$ hyperspectral image after intensity offset adjustment.

For calibration at full illumination state, an optical template with full reflection of white light (i.e., all wavelengths) can be used. For example, the inventors fixed the template in a dark box in which the environment light is completely blocked. Then the LEDs were turned on one by one and one image per spectral band is taken from the template. In a calibrated system, the intensity of all the images must be homogeneous with full brightness value ($I_w$). Any spatial (in-plane) and spectral heterogeneity should be fixed by pixel-wise multiplying of an adjusting matrix $[C_{adj}(i)]$ to the acquired hypercube $[H_{cal}(i)]$. The adjusting matrix is defined as $$\forall i \in \{1, 2, \ldots, N\} : C_{adj}(i) = (i) = I_w / H_{cal}(i).$$

In an 8-bit imaging (with 256 intensity levels), $I_w$ is 255. Hence, during endoscopy:

$$\hat{H} = C_{adj} \cdot \hat{H}_b,$$

where $\hat{H}$ is the calibrated hypercube. The following equation shows the relationship between calibrated hypercube and the original one (before calibration):

$$\forall i \in \{1, 2, \ldots, N\} : \hat{H}(i) = C_{adj}(i) \cdot [H(i) - B].$$

Controlling Sequencing of the LEDs for Different Applications:

The controlling system will provide K≥11 controlling sequencing for different tissues or medical applications, as listed below. Example systems, their spectral range of interests, and their applications are also explained in the following section.

One LED lighting sequence for blood vessel detection
One LED lighting sequence for hemoglobin concentration measure
One LED lighting sequence for nerve detection
One LED lighting sequence for lipid detection
One LED lighting sequence for the skin disease application
One LED lighting sequence for the muscle application
One LED lighting sequence for tongue or other oral cancer detection
One LED lighting sequence for pharynx cancer detection
One LED lighting sequence for esophagus cancer detection
One LED lighting sequence for lung cancer detection
One LED lighting sequence for gastric cancer detection 1) Full Spectrum I:
355 nm to 1450 nm (in order switching from UV to IR)
Application: Melanoma skin lesions (365 nm-800 nm)

2) Full Spectrum II:
355 nm to 1450 nm (switching one LED from one side of the spectrum and the next from the other side and so on so forth to cover the whole spectrum)
Applications: Melanoma skin lesions (365 nm-800 nm) and research purposes 3) Full Spectrum III:
   Sparse illumination from 355 nm to 1450 nm (In each HSE frame one third of LEDs with spectral bands distributed from UV to IR are switched and the full spectrum is covered in three HSE frames as shown following)
   HSE frame #n: LED #1, LED #4, LED #7, . . . , LED #28
   HSE frame #n+1: LED #2, LED #5, LED #8, . . . , LED #29
   HSE frame #n+2: LED #3, LED #6, LED #9, . . . , LED #30
   A machine-learning post-processing step in the external workstation is applied to complete the spectrum.
   Application: Melanoma skin lesions (365 nm-800 nm) and research purposes
4) Infrared (IR):
   700 nm to 1450 nm
   Applications: Gastric cancer (975 nm, 1075 nm, 1215 nm, 1275 nm, 1390, and 1450 nm), Gasteric cancer (1226 nm-1251 nm and 1288 nm-1370 nm), Subcutaneous fat (~930 nm: 925 nm-935 nm, Water and Lipid differentiation (1210 nm), Optic disc, sclera, and lamina cribrosa (>700 nm)
5) Visible:
   410 nm to 700 nm
   Application: Thyroid cancer (450 nm-600 nm)
   Also used for pseudo-RGB imaging to mimic the conventional endoscopy (made in the external workstation)
6) Red:
   610 nm to 700 nm
   Applications: Melanin (600 nm-670 nm), Arterioles (633 nm-700 nm)
7) Green:
   505 nm to 587 nm
   Applications: Hemoglobin (530 nm-600 nm), Superficial venous and arteriolar plexi (540 nm-580 nm), Oxygen saturation in retinal vessels (561 nm), Choroidal vasculature patterns (550 nm)
8) Blue:
   410 nm to 470 nm
   Application: Superficial capillary network (450 nm)
9) Visible-IR (VIR):
   410 nm to 1450 nm
   Applications: Esophagus pre-cancer (600 nm-800 nm), Hemoglobin concentration (625 nm and 770 nm), Large deep vessels (600 nm-970 nm), Oral cavity cancer (450 nm-900 nm)
10) UV:
    355 nm to 395 nm
    Application: Research purposes
11) UV-Visible (UVV):
    355 nm to 690 nm
    In some cases, the body of the device can allow for exchanging micro-LED arrays. That is, the micro-LED array can be replaceable so for each specific application, a micro-LED array can be selected that is customized for the application.
    Application: Research purposes
Experiment V (Ex Vivo Tissue Imaging):
   This experiment was conducted by the inventors using a large-scale HSE system prototype that includes an HSE device and an external workstation. The HSE device and external workstation include all necessary components for HSE imaging described above. Therefore, for brevity, only specific features of the HSE system are discussed with the understanding that the HSE system includes all necessary components for HSE imaging described above. A specific feature of the HSE device used for this experiment is an LED array with LEDs that emit eighteen different wavelengths (e.g., 405, 420, 450, 470, 505, 525, 555, 590, 610, 630, 660, 700, 770, 800, 830, 850, 890, and 910 nm). The HSE device and an imaging target(s) were placed inside a dark box. A moving stage was used in the dark box to adjust the distance between the HSE device and the imaging target. For adjusting the forward voltages of the LEDs, one potentiometer in series with each LED was used. An FPGA was used to control the LEDs. The FPGA general-purpose I/Os are connected to the LEDs' driving board to provide a controlling signal for turning on and off the LEDs. The inventors used a diffuser film in front of the LED array to have a better distribution of the illumination.

The LED's illumination power and distribution as well as the sensitivity of the camera sensor elements can vary. Therefore, an image intensity calibration is required before each experiment to adjust the intensity of the spectral images. The calibration compensates for the spatial and spectral inhomogeneity of the LEDs' illuminations and the spatial inhomogeneity in camera sensors. For calibration, the inventors needed to ensure that (1) there is no intensity recorded when there is no light (black image) and the reflected intensity from a white reference is uniform and at the highest level (white) when each of the LEDs is on. For L spectral bands (here L=18), the calibrated image, $\hat{I}(x,y,\lambda)$, after canceling out the intra-wavelength inhomogeneous illumination distribution as well as inter-wavelength illumination inconsistency is given as:

$$\hat{I}(x, y, \lambda) = \frac{I(x, y, \lambda) - I_D(x, y)}{I_W(x, y, \lambda) - I_D(x, y)}, \lambda \in \{1, 2, 3, \ldots, L\}$$

where for each pixel (x,y), $I(x,y,\lambda)$ is the reflection intensity of the $\lambda^{th}$ band of the hypercube before calibration, $I_D(x,y)$ is the reflection intensity of the black image captured when all the LEDs are off, and $I_W(x,y,\lambda)$ is the reflection intensity of the $\lambda^{th}$ band when a white reference is used as the target.

For evaluating the performance of hyperspectral imaging using LED-based illumination, the inventors designed a set of experiments on ex vivo tissues. The inventors captured images of the tissues using a customized HSI camera system as a reference. The reference camera covered 150 wavelengths from 470 nm to 900 nm with about 2.886 nm spectral resolution. The inventors compared the acquired spectral images to the reference hyperspectral image. For the ex vivo imaging, the inventors used normal tissues taken from different animal models including chicken (drumstick), lamb (brain, heart, liver, and kidney), and two mice (heart, liver, left and right kidneys). The inventors also used four neuroblastoma cancerous tumors from two mice for the ex vivo imaging. Before starting the experiments, the inventors first captured an image with all the LEDs off and then captured images from a white reference for calibration purposes. For capturing images from each ex vivo tissue, the inventors put the tissue on the stage inside the dark box and sealed the box to block the environmental light. Then the inventors turned the first LED on for 2 seconds, captured the images, and turned off the LED. With a delay of DT (here 2 seconds) the second LED was turned on. The inventors continued to turn on and off the LEDs one by one and capture images. The pulse width (PW) of the signals was set to 2 seconds.

For each tissue, the inventors calibrated the images captured by the HSE system and the reference camera and then registered the images of the reference camera to the images captured by the HSE system. Then, the inventors segmented the tissues automatically to remove the background and the glares of the images on each pair of hypercubes using histogram analysis. The inventors combined the two segmentation masks by using the overlap between them to make a segmentation label of the glare-free tissue regions on both hypercubes as the common ROI for further processing. The inventors extracted the spectral signatures of the tissues from the ROIs. To have a better comparison between the two systems, the inventors normalized the spectral signatures using the following equation:

$$\hat{S}(\lambda) = \frac{S(\lambda) - S_{min}}{S_{max} - S_{min}},$$

where $S(\Delta)$ is the original spectral signature at wavelength $\Delta$, $S_{min}$ and $S_{max}$ are the minimum and maximum values of $S(\lambda)$, respectively, and $\hat{S}(\lambda)$ is the normalized spectral signature.

Figure 15:
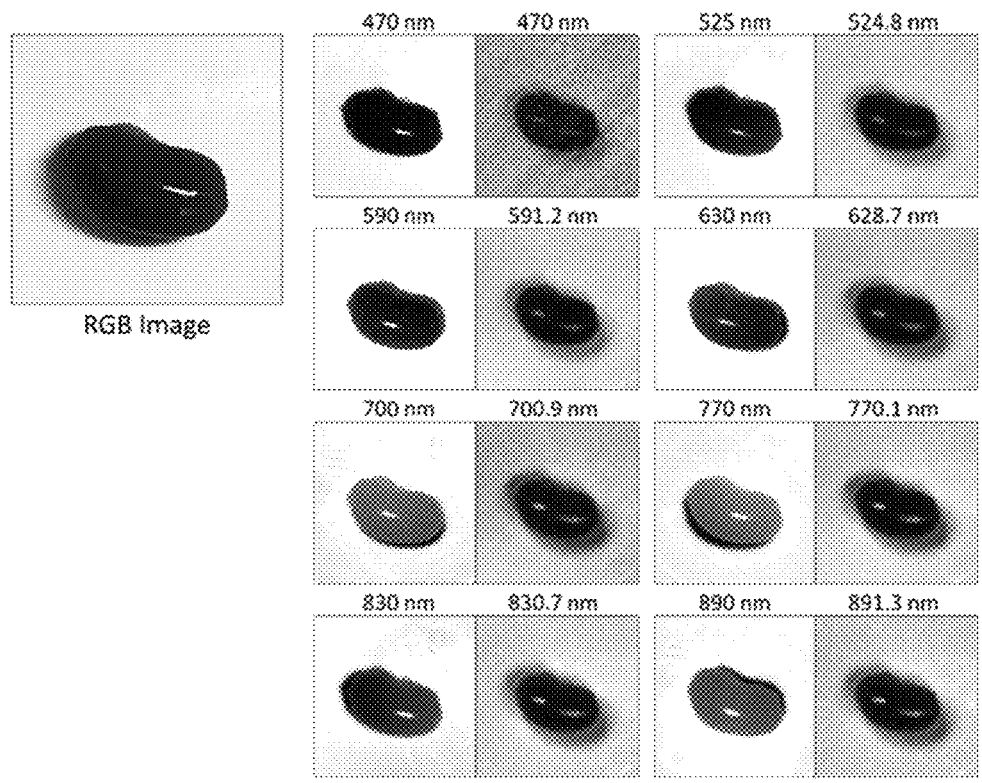
FIGS. 15-18 illustrate the captured images from four selected ex vivo tissues including a normal mouse kidney, a normal mouse liver, a normal lamb brain, and a neuroblastoma tumor resected from a mouse model.
Figure 16:
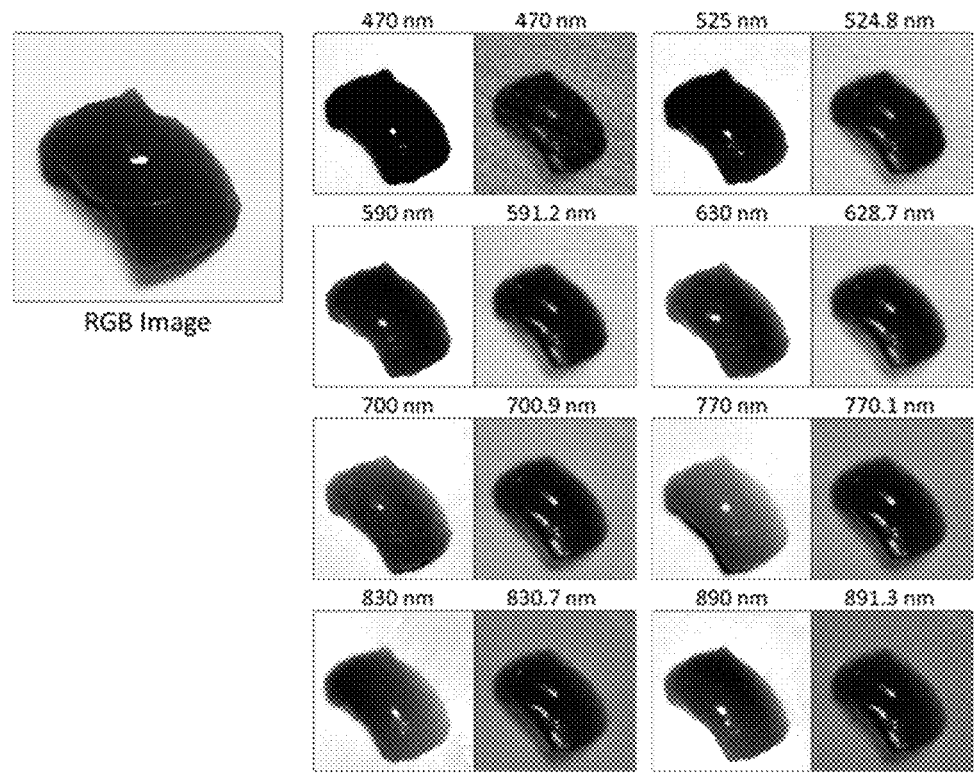
Figure 17:
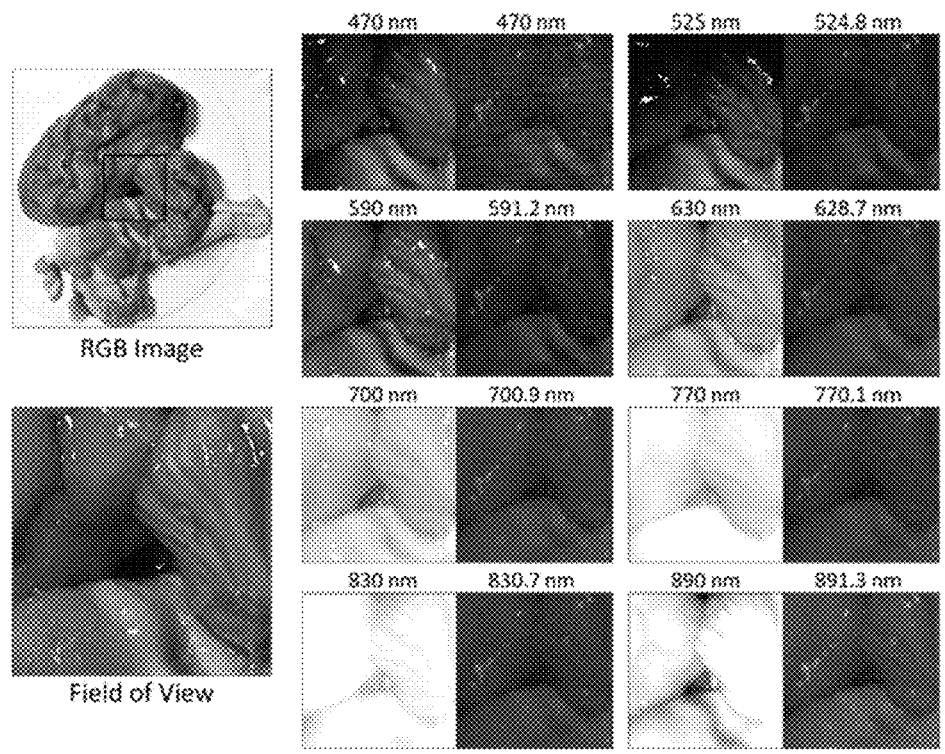
Figure 18:
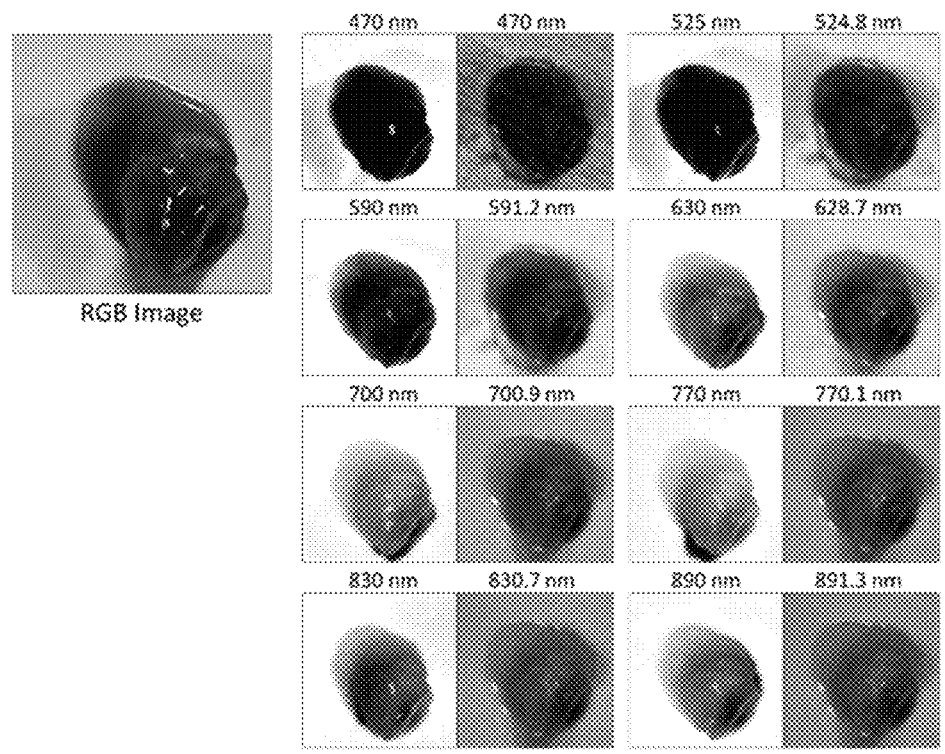

FIG. 14 illustrates captured images of all 18 spectral channels utilizing the HSE device from the white template before (images on the left) and after (images on the right) calibration. FIG. 15 illustrates images of a normal mouse kidney captured using the HSE system (images on the left) and images of the normal mouse kidney captured using the reference HSI camera (images on the right), with the captured images from both the HSE system and the reference HSI camera using approximately the same eight spectral bands. FIG. 16 illustrates images of a normal mouse liver captured using the HSE system (images on the left) and images of the normal mouse liver captured using the reference HSI camera (images on the right), with the captured images from both the HSE system and the reference HSI camera using approximately the same eight spectral bands. FIG. 17 illustrates images of a normal lamb brain captured using the HSE system (images on the left) and images of the normal lamb brain captured using the reference HSI camera (images on the right), with the captured images from both the HSE system and the reference HSI camera using approximately the same eight spectral bands. FIG. 18 illustrates images of a neuroblastoma tumor resected from a mouse model captured using the HSE system (images on the left) and images of the neuroblastoma tumor resected from a mouse model captured using the reference HSI camera (images on the right), with the captured images from both the HSE system and the reference HSI camera using approximately the same eight spectral bands.

Figure 19A:
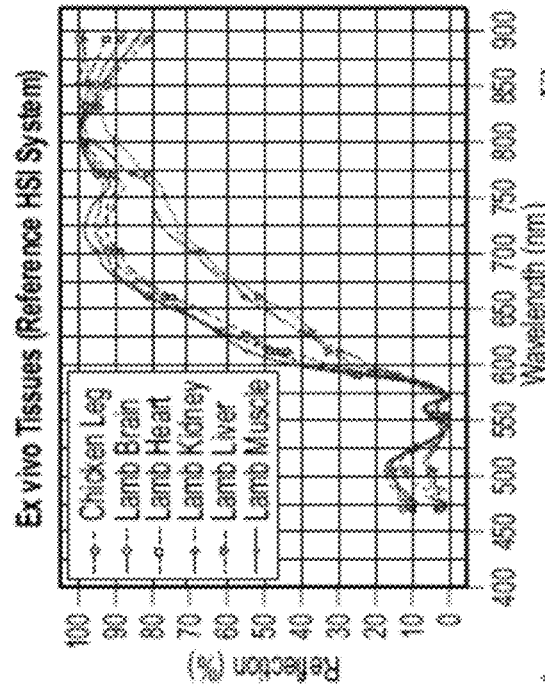
FIGS. 19A and 19B illustrate spectral signatures of normal lamb and chicken tissues using the HSE system and the reference HSI camera.
Figure 19B:
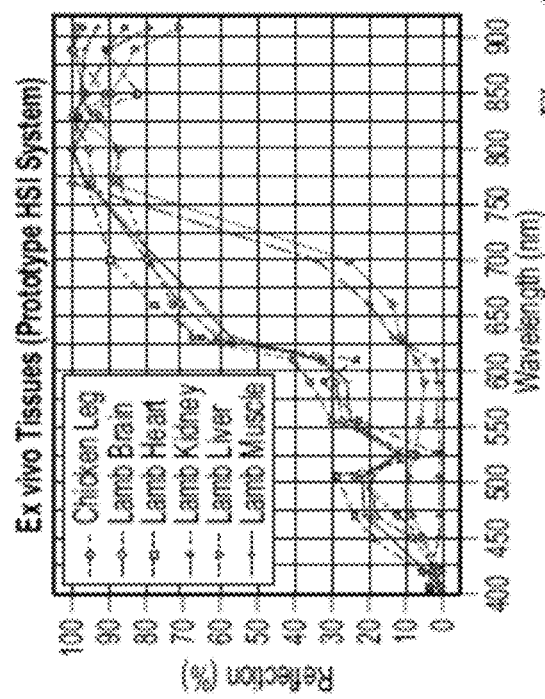
Figure 20A:
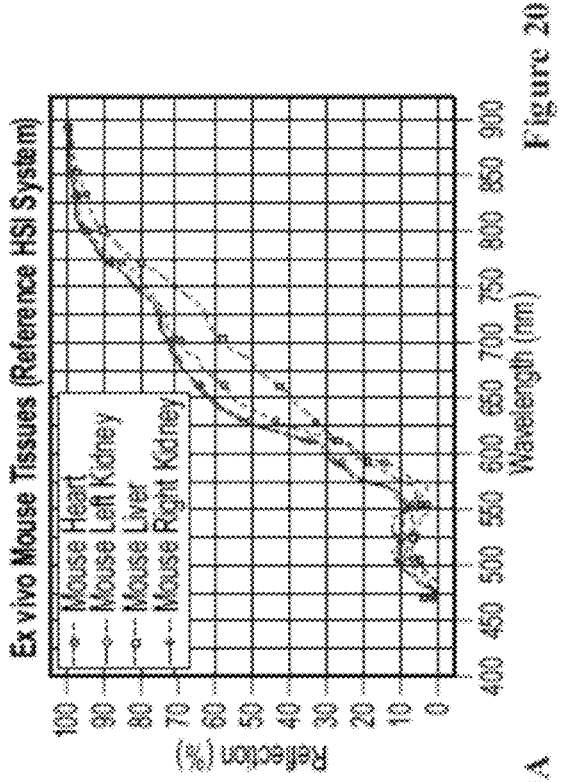
FIGS. 20A and 20B illustrate spectral signatures of normal mouse tissues using the HSE system and the reference HSI camera.
Figure 20B:
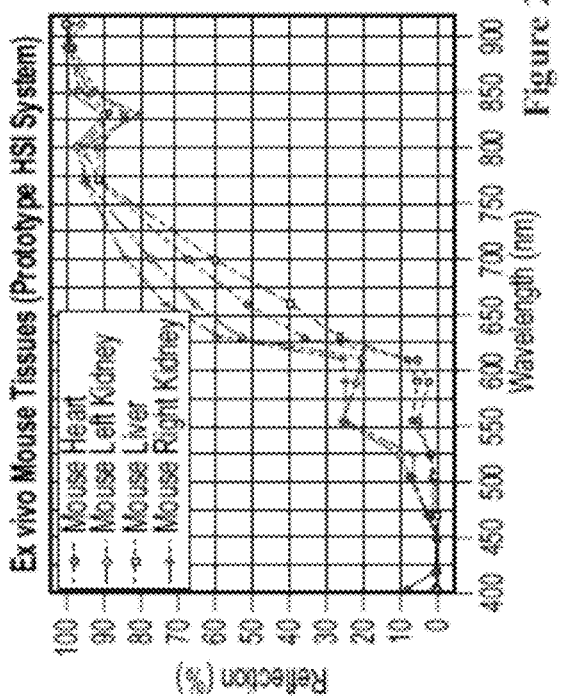
Figure 21A:
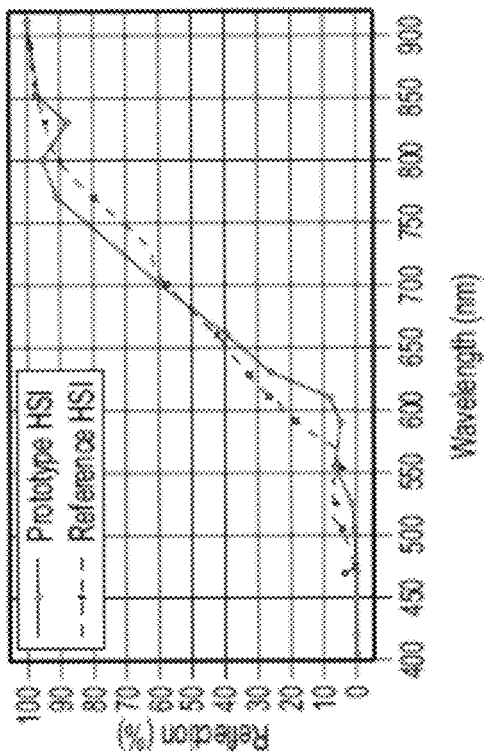
FIGS. 21A-21D illustrate comparisons between hyperspectral images of the HSE system and the reference HSI camera for the four sample tissues illustrated in FIGS. 15-18.
Figure 21B:
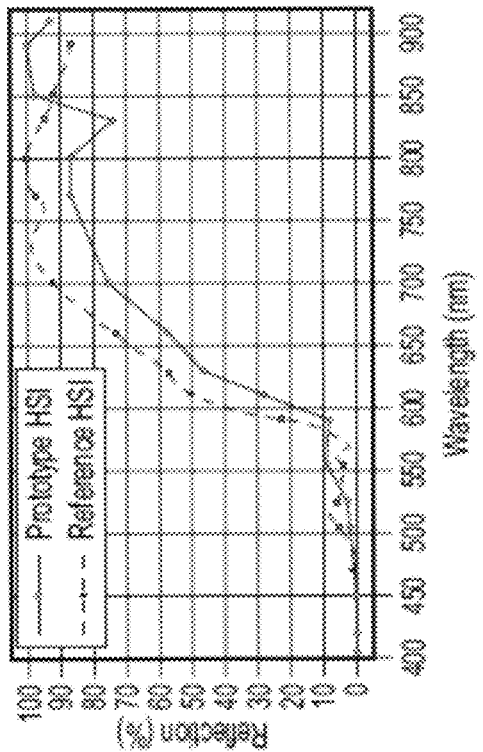
Figure 21C:
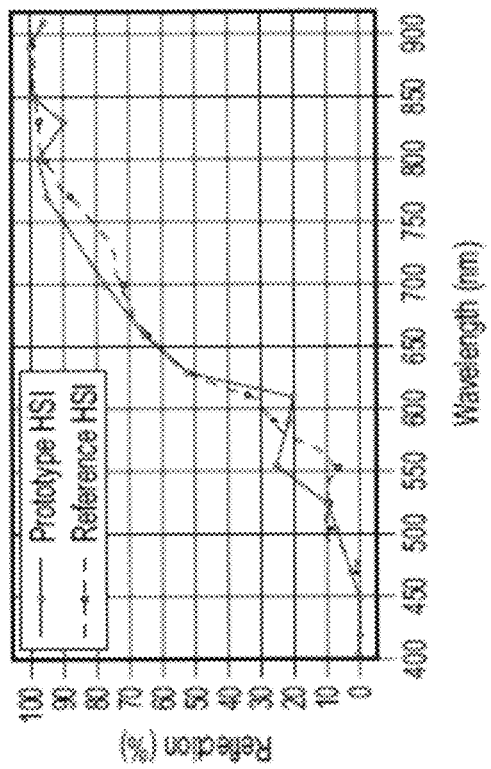
Figure 21D:
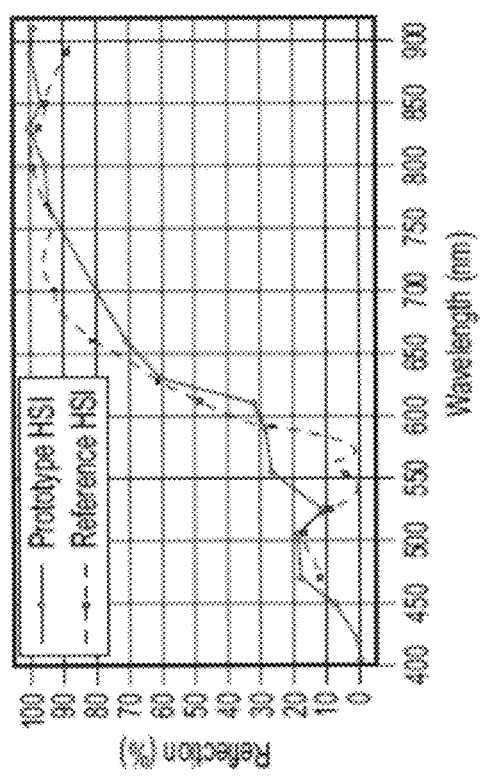
Figure 22A:
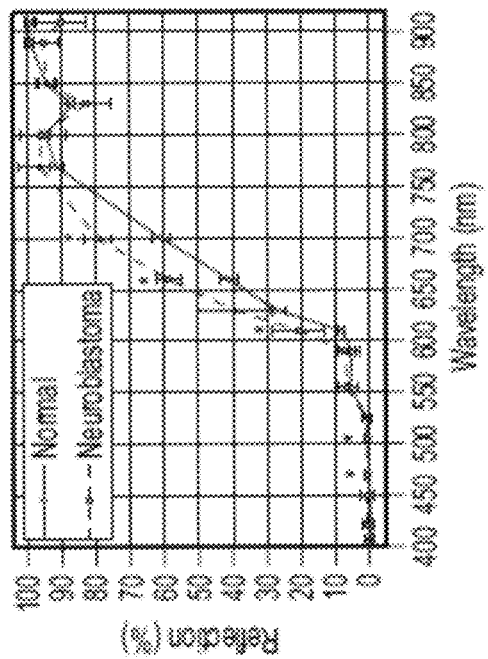
FIGS. 22A-22D illustrate a statistical comparison of the spectral signatures of normal animal tissues versus cancerous animal tissues.
Figure 22B:
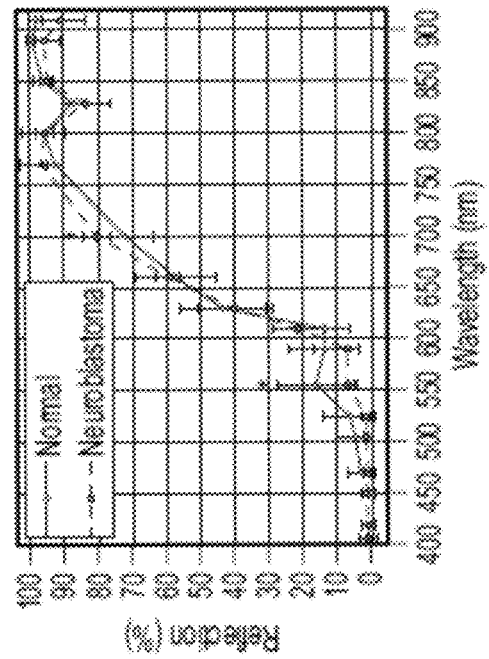
Figure 22C:
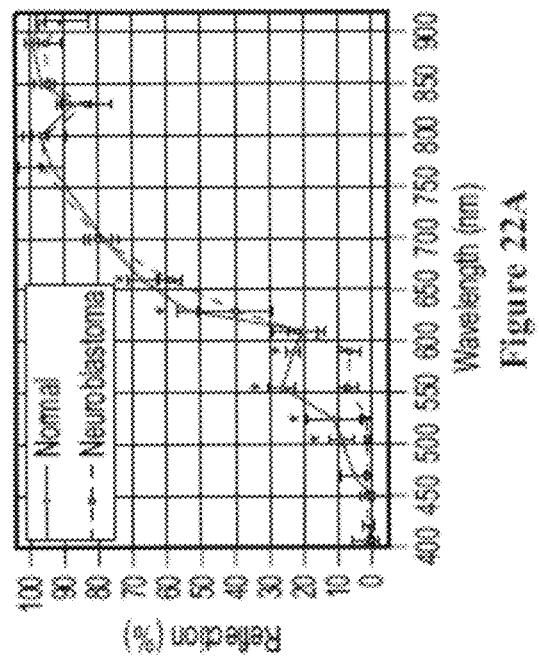
Figure 22D:
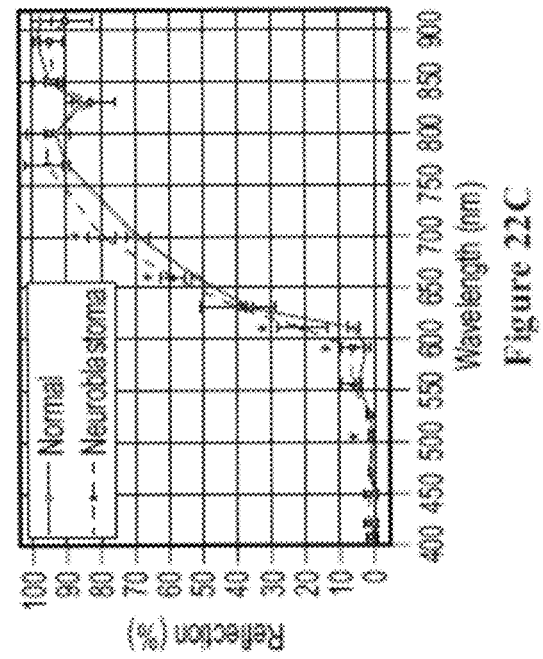

FIGS. 19A and 19B illustrate spectral signatures of normal lamb and chicken tissues using the HSE system (FIG. 19A) and the reference HSI camera (FIG. 19B). FIGS. 20A and 20B illustrate spectral signatures of normal mouse tissues using the HSE system (FIG. 20A) and the reference HSI camera (FIG. 20B). FIGS. 21A-21D illustrate comparisons between hyperspectral images of the HSE system and the HSI camera for the four sample tissues illustrated in FIGS. 15-18. FIG. 22A illustrates a comparison of the spectral signatures of a normal mouse kidney to a neuroblastoma tumor using one-tailed t-tests with a significance threshold of 0.05. FIG. 22B illustrates a comparison of the spectral signatures of a normal mouse liver to a neuroblastoma tumor using one-tailed t-tests with a significance threshold of 0.05. FIG. 22C illustrates a comparison of the spectral signatures of a normal mouse heart to a neuroblastoma tumor using one-tailed t-tests with a significance threshold of 0.05. FIG. 22D illustrates a comparison of the spectral signatures of a normal mouse tissues (e.g., two mouse hearts, four mouse kidneys, and two mouse livers from two healthy mice) to neuroblastoma tumors (e.g., four neuroblastoma tumors from two mice) using one-tailed t-tests with a significance threshold of 0.05. Asterisks in FIGS. 22A-2D show the spectral channels with statistically significant differences between normal and cancerous tissues (e.g., $p<0.05$).

Results show that the performance of the HSE system is comparable to a commercial HSI camera system. FIGS. 15-18 illustrate that the HSE system can capture images with comparable quality when compared to a commercial HSI system. At lower wavelengths like 470 nm, the quality of images of the HSE system is even higher than the reference HSI camera. FIGS. 19A, 19B, 20A, and 20B show the capability of the HSE system in differentiating between different tissues similar to the reference HSI camera. FIGS. 22A-22C show that the HSE system can differentiate between normal and cancerous tissues. The inventors detected statistically significant differences between normal and cancer at many spectral bands. FIG. 22D shows that at 555 nm and 700 nm there is a statistically significant difference between cancer and normal tissues.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A miniaturized hyperspectral imaging device providing imaging in rapid or real-time, comprising:
   a body;
   a camera within the body;
   a micro-LED array arranged around the camera within the body, the micro-LED array including micro-LEDs of varying spectral bands, wherein the micro-LED array is configured to provide a spectral resolution of at least five discrete spectral bands; and
   an imaging controller within the body and coupled to the camera and the micro-LED array, wherein the imaging controller provides LED timing information and LED intensity information to the micro-LED array,
   wherein the miniaturized hyperspectral imaging device is configured to be inserted inside a patient's body.

2. The device of claim 1, wherein the imaging controller further provides camera timing information to the camera for indicating when to capture an image.

3. The device of claim 2, wherein spatial resolution of the image is at least 0.05 millimeters.

4. The device of claim 1, further comprising a transceiver within the body, wherein the transceiver transmits image data captured by the camera to an external workstation.

5. The device of claim 1, wherein the LED timing information provided by the imaging controller to the micro-LED array comprises a timing signal to each micro-LED of the micro-LED array, each timing signal having a pulse.

6. The device of claim 5, wherein each timing signal is equal to or less than ten milliseconds.

7. The device of claim 5, wherein the LED intensity information provided by the imaging controller to the micro-LED array comprises a corresponding pulse duration of the pulse for each timing signal.

8. The device of claim 5, wherein the LED intensity information provided by the imaging controller to the micro-LED array comprises a particular forward voltage for each timing signal.

9. The device of claim 5, wherein a time delay between a first timing signal sent to a first micro-LED of the micro-LED array and a subsequent timing signal sent to a second micro-LED of the micro-LED array is optimized for minimum time and minimum interference between illuminations of LEDs.

10. The device of claim 1, wherein an imaging rate of the device includes at least twenty frames per second for each varying spectral band of the micro-LED array.

11. The device of claim 10, wherein the micro-LED array includes micro-LEDs having at least eight varying spectral bands, wherein each micro-LED emits a discrete spectral band.

12. The device of claim 11, wherein an outer diameter of the micro-LED array is less than or equal to thirty millimeters.

13. The device of claim 1, wherein each micro-LED in the micro-LED array includes a surface area of less than or equal to four millimeters squared.

14. The device of claim 1, wherein the body is configured as an endoscope.

15. The device of claim 1, wherein the body is configured as a laparoscope.

16. The device of claim 1, wherein the body is configured as a handheld device.

17. A method for controlling an imaging device, comprising:
providing LED timing information and LED intensity information to a micro-LED array, the micro-LED array including micro-LEDs of varying spectral bands, wherein the micro-LED array is configured to provide a special resolution of at least five discrete bands, the LED timing information comprising a timing signal to each micro-LED of the micro-LED array, each timing signal having a pulse;
providing camera timing information to a camera of the imaging device for capturing a plurality of images, wherein an image of the plurality of images is captured for a time period associated with each timing signal, wherein the imaging device is configured to be inserted inside a patient's body; and
receiving the plurality of images from the camera.

18. The method of claim 17, further comprising sending, via a transceiver, the plurality of images to an external workstation.

19. The method of claim 17, wherein each timing signal is equal to or less than ten milliseconds.

20. The method of claim 17, wherein a time delay between a first timing signal sent to a first micro-LED of the micro-LED array and a subsequent timing signal sent to a second micro-LED of the micro-LED array is optimized for minimum time and minimum interference between illuminations of micro-LEDs.

* * * * *